(12) United States Patent
Kokolis

(10) Patent No.: US 10,154,813 B1
(45) Date of Patent: Dec. 18, 2018

(54) METHOD AND APPARATUS FOR PATIENT SKIN COLOR MONITORING AND DRUG EFFICACY MEASUREMENT

(71) Applicant: Spyros Kokolis, Brooklyn, NY (US)

(72) Inventor: Spyros Kokolis, Brooklyn, NY (US)

(*) Notice: Subject to any disclaimer, the term of this patent is extended or adjusted under 35 U.S.C. 154(b) by 0 days.

(21) Appl. No.: 16/015,057

(22) Filed: Jun. 21, 2018

Related U.S. Application Data

(63) Continuation-in-part of application No. 15/809,592, filed on Nov. 10, 2017, and a continuation-in-part of application No. 15/641,045, filed on Jul. 3, 2017.

(51) Int. Cl.
| | |
|---|---|
| *A61B 5/00* | (2006.01) |
| *A61B 5/026* | (2006.01) |
| *A61B 5/103* | (2006.01) |
| *A61B 5/02* | (2006.01) |
| *A61K 49/00* | (2006.01) |

(52) U.S. Cl.
CPC .......... *A61B 5/4848* (2013.01); *A61B 5/0075* (2013.01); *A61B 5/02* (2013.01); *A61B 5/0261* (2013.01); *A61B 5/1032* (2013.01); *A61B 5/4839* (2013.01); *A61B 5/4884* (2013.01); *A61K 49/0006* (2013.01)

(58) Field of Classification Search
None
See application file for complete search history.

(56) References Cited

U.S. PATENT DOCUMENTS

| | | | |
|---|---|---|---|
| 4,109,643 A | 8/1978 | Bond | |
| 4,241,738 A | 12/1980 | Lubbers | |
| 4,798,464 A | 1/1989 | Boostrom | |
| 5,043,571 A | 8/1991 | Hasegawa | |
| 5,297,555 A | 3/1994 | Martens | |
| 5,402,778 A | 4/1995 | Chance | |
| 5,564,417 A | 10/1996 | Chance | |
| 5,671,735 A | 9/1997 | MacFarlane et al. | |
| 6,011,985 A | 1/2000 | Athan | |
| 6,076,010 A | 6/2000 | Boas | |
| 6,132,380 A | 10/2000 | Cohen | |
| 6,437,866 B1 | 8/2002 | Flynn | |
| 6,993,167 B1 | 1/2006 | Skladnev | |
| 6,997,882 B1 | 2/2006 | Parker | |

(Continued)

OTHER PUBLICATIONS

Furchgott, Robert F., The Nature of the Endothelium-Derived Relaxing Factor, www.hscbklyn.edu.

(Continued)

*Primary Examiner* — Katherine Fernandez
*Assistant Examiner* — Michael Kellogg
(74) *Attorney, Agent, or Firm* — Notaro, Michalos & Zaccaria P.C.

(57) ABSTRACT

Methods and apparatus for determining the efficacy of a drug by diagnosing cardiovascular health in a patient by monitoring changes in skin redness levels, which is associated with perfusion and ability of circulatory system to adapt to physical exertion. Color detectors including colorimeters and spectrophotometers may be used to monitor and quantify skin color. Wet run solutions such as acetylcholine solutions may be applied to the skin area being monitored. Skin redness can be monitored during the course of exercise or a stress test, as well as during recovery. Wearable color detector devices can be worn by patients during exercise.

16 Claims, 19 Drawing Sheets

(56) References Cited

U.S. PATENT DOCUMENTS

| | | | |
|---|---|---|---|
| 7,008,350 | B1 | 3/2006 | Yamazaki |
| 7,483,733 | B2 | 1/2009 | Shani |
| 7,620,212 | B1 | 11/2009 | Allen et al. |
| 8,082,015 | B2 | 12/2011 | Yodh |
| 8,208,997 | B2 | 6/2012 | Nilsson |
| 8,236,516 | B2 | 8/2012 | Evelegh |
| 8,712,491 | B2 | 4/2014 | Evelegh |
| 8,948,832 | B2 | 2/2015 | Hong |
| 9,113,832 | B2 | 8/2015 | Al-Ali |
| 2004/0044080 | A1 | 3/2004 | Place |
| 2011/0106201 | A1* | 5/2011 | Bhunia ............... A61B 5/1459 607/18 |
| 2014/0378779 | A1* | 12/2014 | Freeman ............ A61B 5/0051 600/301 |
| 2015/0335288 | A1* | 11/2015 | Toth ................... A61B 5/6833 600/373 |
| 2016/0073886 | A1 | 3/2016 | Connor |

OTHER PUBLICATIONS

Furchgott, Robert F., Endothelium-Derived Relaxing Factor: Discovery, Early Studies, and Identification as Nitric Oxide, Noble Lecture—Health Science Center, Brooklyn, NY, Dec. 8, 1998.

Topical Non-Iontophoretic Application of Acetylcholine and Nitroglycerin via a Translucent Patch: A New Means for Assessing Microvascular Reactivity by Robert B. Schonberger et al. pub. Yale Journal of Biology and Medicine 79 (2006), pp. 1-7.

Bruce protocol by Wikipedia, pub. on line on Jan. 16, 2017 at <https://en.wikipedia.org/w/index.php?title=Bruce_protocol&oldid=760437118>.

Pulse oximetry by Wikipedia, pub. on line on Jun. 2, 2016 at <https://en.wikipedia.org/w/index.php?title=Pulse_oximetry&oldid=723407047>.

* cited by examiner

METHOD AND APPARATUS FOR PATIENT SKIN COLOR MONITORING AND DRUG EFFICACY MEASUREMENT

CROSS-REFERENCE TO RELATED APPLICATIONS

This application is a continuation-in-part application and claims priority to U.S. Application Ser. No. 15/641,045, filed Jul. 3, 2017, and Ser. No. 15/809,592, filed Nov. 10, 2017, the contents of which are herein incorporated by reference in their entirety.

FIELD AND BACKGROUND OF THE INVENTION

The present invention relates generally to the field of health and medicine, and in particular to a new and useful spectrophotometric colorimeter methods and apparatus determine the efficacy of a drug, by measuring and storing the color of a subject's skin over time for tracking and diagnosing aspects of the subject's cardiovascular condition.

In physiology, "perfusion" is the process of a body delivering blood to capillary beds in living tissues. As more or less blood is delivered to capillaries near a skin surface, the color of the skin changes. For example, skin having more blood delivered near the surface is more red than skin on the same individual having less blood. Aspects of the work leading to this invention have determined that changes in skin color and perfusion will be greater for patients in better cardiovascular health, and smaller for patients who are not in good cardiovascular health, for a given stimulus.

Endothelium is a type of epithelium that lines the interior surface of blood vessels and lymphatic vessels. It is a thin layer of simple squamous cells called endothelial cells. Vascular endothelial cells line the entire circulatory system, from the heart to the smallest capillaries. Endothelium of the interior surfaces of the heart chambers is called endocardium. Endothelial dysfunction is linked to various vascular diseases, and is often regarded as a key early event in the development of atherosclerosis. Impaired endothelial function, which can cause hypertension and thrombosis, is often seen in patients with coronary artery disease, diabetes mellitus, hypertension, hypercholesterolemia, and in smokers. Endothelial dysfunction is also correlated with future adverse cardiovascular events.

In blood vessels, vascular smooth muscle cells are behind the endothelial cells, the endothelial cells forming a thin layer between the blood and the muscle cells. Vascular smooth muscle contracts or relaxes to change both the diameter of blood vessels and, as a result, the local blood pressure. Arteries have more smooth muscle than veins, and so generally have greater thickness. Endothelial cells affect the movement of substances (such as nitric oxide) from the blood to the vascular smooth muscle cells which, in turn, dilate and contract the vessel. Proper functioning of the vascular endothelium and vascular smooth muscle cells, together, is important for fast end effective physiological response to stresses such as exercise.

Nitric oxide is an important signaling molecule involved in various physiological and pathological processes. Of particular relevance here, nitric oxide is a powerful vasodilator which has a very short half-life in the blood. Nitroglycerine and amyl nitrite, used to treat heart conditions, are precursors of nitric oxide.

The vascular endothelium could be considered the largest organ in the human body: the area inside the lungs alone can have a surface area of over 3,500 square feet, larger than a tennis court. Oxygen, carbon dioxide, and other important substances pass through the endothelium in the lungs, blood vessels, and elsewhere, making it important in regulating homeostasis. Hormones and other vasoactive substances affect the functioning of the endothelium. For example, the permeability of the vascular endothelium varies in response to oxygen levels, hormones, and other stimuli.

The endothelium has a variety of functions. Endothelium plays a role in controlling vascular tone—i.e. the degree of constriction or dilation. This, in turn, affects blood pressure and blood flow. It is a physiological barrier which regulates the flow of substances into and out of the vasculature. Some of these substances, in turn, affect vessel wall phenotype. Vascular endothelial cells also act as signal transducers between the blood and other cells (e.g. smooth muscle cells). Vascular endothelial cells are involved in fluid filtration and hormone trafficking. It is involved in the removal and biotransformation of many drugs. It participates in immune responses, such as by binding immune complexes and immunological blood components.

Alterations to endothelium has been found to be a precursor to other conditions. For example, changes to the endothelium have been identified as precursors of diabetes linked atherosclerosis.

The endothelium is regulated by vasoactive compounds such as angiotensin II, prostacyclin, thromboxane A2, nitric oxide (NO), and endothelins. It can also produce and release vasoactive compounds. It is also affected by the expression and activity of enzymes such as angiotensin converting enzyme, endothelin converting enzyme, nucleotidases, NO synthase, and lipoprotein lipase. Disease states, in turn, can affect the ability of these mediators to control the vasculature normally.

Vasodilation is a term for the widening of blood vessels. Vasodilation results from relaxation of smooth muscle cells in the vessel walls, particularly in the large veins, large arteries, and smaller arterioles. The opposite of vasodilation is vasoconstriction, i.e. the narrowing of blood vessels. When blood vessels dilate, blood flow increases due to a decrease in vascular resistance. This also typically decreases blood pressure. Vasodilation and vasoconstriction response may be intrinsic (due to local processes or stimuli) or extrinsic (due to circulating hormones or the nervous system). In some cases, vasodilation and constriction are systemic —i.e. occurring simultaneously throughout the circulatory system. Substances that cause vasodilation are called vasodilators. Vascular dilation decreases endothelial "resistance" to blood flow by opening a wider passage for the blood. Constriction, in turn, increases resistance by narrowing the passage.

Dr. Robert Furchgott (1916-2009) was a Nobel Prize-winning American biochemist who contributed to the identification of nitric oxide as a transient cellular signal in mammals. His publicly available Nobel Prize lecture publication outlines his work in this area and provides useful background. *Endothelium-Derived Relaxing Factor: Discovery, Early Studies, and Identification as Nitric Oxide*, Robert F. Furchgott, Dec. 8, 1998.

Aspects of the work leading to this invention have determined that observations of vascular endothelium in blood capillaries supplying the skin provide information regarding the vascular endothelium elsewhere, such as in the same individual's heart.

Reflected color can be measured using a spectrophotometer, which typically makes measurements in the visible light region of a given color sample. Spectrophotometry uses photometers that can measure a light beam's intensity as a function of its color or wavelength. If, for example, readings are made at 10 nanometer increments, the visible light range of 400-700 nm will yield 31 readings. These readings can be used to draw a reflectance curve illustrating how much light of each wavelength is reflected, as a function of wavelength.

Colorimeters are an alternative to spectrophotometers. Colorimeters typically make a limited number of wideband spectral energy readings along the visible spectrum by using filtered photodetectors.

The generic term "color detector" refers to spectrophotometers, colorimeters, and their functional equivalents which are capable of detecting and quantifying at least red wavelengths.

The Konica Minolta CM 700d spectrophotometer is a handheld unit that is capable of accurately quantifying the color of a surface. It is a large unit, however, that is not suitable to be worn like a wristwatch. U.S. Pat. No. 5,043,571, originally assigned to Minolta Camera KK, discloses a color CCD based spectrophotometer that is amenable to miniaturization, however.

Colors can be defined numerically, and differences between two colors can also be calculated and defined numerically. Several quantitative color systems exist, and can be adapted for use with this invention.

One available system is the L*a*b* color space or Hunter L/a/b color space, which can be visualized as a rectangular 3D coordinate system. L indicates lightness, a is the red/green coordinate, and b is the yellow/blue coordinate. L can have a value from 0 (black) to 100 (perfect reflection). The a and b axes have no numerical limits. Coordinate a is positive when red, and negative when green. Positive b is yellow, and negative b is blue. Colors can be described numerically using numerical values for L, a, and b. Differences between two colors can be quantified for each of the individual L/a/b values ($\Delta L$, $\Delta a$, $\Delta b$). Overall differences between two colors can be derived numerically based on the three $\Delta$ values.

An alternative system, L*C*h color space, uses cylindrical instead of rectangular coordinates. In this system, L indicates lightness, C represents chroma, and h is the hue angle. Chroma and hue are calculated from the a and b coordinates of the L/a/b color space.

Patients with coronary artery blockages may have minimal symptoms and an normal electrocardiogram (ECG) while at rest. Cardiac stimulation may be necessary to identify irregularities. A cardiac "stress test" measures the body's ability to respond to external stress in a controlled clinical environment. The stress response is typically induced by exercise. The stress of exercise can also be approximated using pharmaceutical stimulation (e.g. dobutamine or adenosine) for patients who cannot easily perform physical exercises.

Cardiac stress tests compare the coronary circulation while the patient is at rest versus the same patient's circulation during maximum physical exertion. The purpose is to identify any abnormal blood flow to the myocardium (heart muscle tissue). This can in turn be a reflection of the overall physical condition of the patient. Stress tests can be used to diagnose coronary artery disease, and to assess patient prognosis after a heart attack.

Cardiac stress tests involve heart stimulation, either by exercise on a treadmill, arm ergometer, exercise bicycle, or with pharmacological stimulation. The stress test is traditionally conducted with the patient connected to an ECG, and in some cases also an imaging device such as an echocardiograph. An ECG shows heartbeat speed and rhythm (steady or irregular). It also detects the strength and timing of electrical signals as they pass through the heart. During a standard stress test, blood pressure is also checked. Patients may be asked to breathe into a tube during the test to monitor breathing and gas exchange. A standard stress test shows changes in heart electrical activity, and whether the heart is getting enough blood during exercise.

In imaging stress tests, pictures are also taken of the heart during exercise and recovery. Imaging stress tests can show how well blood is flowing in the heart, valve function, and how effectively the heart pumps blood when it beats. Imaging stress tests often use echocardiography (echo). Echocardiography uses sound waves to create a moving picture of the heart. A stress test echocardiogram can show areas of poor blood flow in the heart, dead heart muscle tissue, and areas of the heart muscle wall which are contracting poorly (e.g. due to heart attack damage or insufficient blood flow). Imaging stress tests using radioactive dye are also available. Imaging stress tests are generally considered better at identifying heart disease than non-imaging tests, but are more costly.

Over the course of a stress test the level of mechanical stress is progressively increased, such as by increasing exercise resistance and/or speed. The technician or attending physician monitors outward symptoms and blood pressure response. Exercise may continue until the patient indicates that they wish to stop, or until a "peak exercise" threshold is attained. In the widely used Bruce Protocol (see below), peak exercise is defined by patient heart rate. Specifically, by subtracting the patient's age from 220 and multiplying the result by 85%. ([220–Age (years)]*0.85=Peak Heart Rate (in beats per minute)). Patients in poor cardiovascular health will typically reach their peak exercise heart rate relatively quickly during exercise. Fit patients require more strenuous exercise to reach a given heart rate.

The Bruce protocol is a particular diagnostic stress test used in the evaluation of cardiac function, developed by Dr. Robert Bruce. A Bruce protocol stress test involves walking on a treadmill while the heart is monitored by an electrocardiograph with electrodes attached to the body. Ventilation volumes and respiratory gas exchanges are also monitored before, during, and after exercise. Treadmill speed and inclination are increased over the course of the test (e.g. every three minutes) until the patient signals that they need to stop. Typically, during a Bruce Protocol, heart rate and perceived exertion are taken every minute, and blood pressure is measured at the end of each stage (i.e. every three minutes).

Doctors commonly classify patient heart failure according to the severity of their symptoms. One common system is the New York Heart Association (NYHA) Functional Classification. It places patients in one of four categories based on how much they are limited in their physical activity. Class I: No limitation of physical activity. Ordinary physical activity does not cause undue fatigue, palpitation, dyspnea (shortness of breath). Class II: Slight limitation of physical activity. Comfortable at rest. Ordinary physical activity results in fatigue, palpitation, dyspnea (shortness of breath). Class III: Marked limitation of physical activity. Comfortable at rest. Less than ordinary activity causes fatigue, palpitation, or dyspnea. Class IV: Unable to carry on any physical activity without discomfort. Symptoms of heart failure at rest. If any physical activity is undertaken, discomfort increases.

Acetylcholine is believed to dilate normal blood vessels by promoting the release of a vasorelaxant substance from the endothelium (endothelium-derived relaxing factor). *Paradoxical Vasoconstriction Induced by Acetylcholine in Atherosclerotic Coronary Arteries*, P L Ludmer et al., N Engl J Med. 1986 Oct. 23; 315(17):1046-51. This article reports that in each of four normal coronary arteries, acetylcholine caused a dose-dependent dilation from a control diameter of 1.94+/−0.16 mm to 2.16+/−0.15 mm with the maximal acetylcholine dose (P less than 0.01). In contrast, all eight of the arteries with advanced stenosis showed dose-dependent constriction, from 1.05+/−0.05 to 0.32+/−0.16 mm at the highest concentration of acetylcholine (P less than 0.01), with temporary occlusion in five. Five of six vessels with minimal disease also constricted in response to acetylcholine. All vessels dilated in response to nitroglycerin, however. The study concluded that paradoxical vasoconstriction induced by acetylcholine occurs early as well as late in the course of coronary atherosclerosis. The findings suggested that abnormal vascular response to acetylcholine is indicative of a defect in endothelial vasodilator function, and may be important in the pathogenesis of coronary vasospasm. Related principles are understood to underlie the "wet run" protocol, described below.

Published Patent application US 2014/0378779 (Freeman et al.) discloses computer-based systems and techniques for analyzing skin coloration using spectral imaging to determine a medical condition of an individual. Freeman also teaches providing feedback to a rescuer or other medical professional based on the colorimetric properties of the patient's skin. Freeman Abstract and paragraph [0002].

Freeman discloses measuring skin color as quantified using an L/a/b color scale. Freeman FIG. 6, paragraphs [0093]-[0097], etc. It also teaches that a spectrophotometer can be used to monitor the color of patient skin surfaces, among other possible devices. Freeman [0085], [0097]. Obtaining the color information can include obtaining baseline colorimetric properties based on an intensity of light radiation reflected from the individual's skin, applying a stimulus configured to produce a change in the colorimetric properties of the individual's skin, and obtaining one or more additional measurements of the colorimetric properties at times selected to capture changes in the colorimetric properties of the individual's skin based on the applied stimulus.

U.S. Pat. No. 7,620,212 (Allen et al.) relates to electro-optical sensors for use in biometric analysis of optical spectra of tissue. Allen 1:52-1:56. Devices according to Allen can include a number of forms having a variety of functions. Allen largely focuses on using biometric methods to determine individual identities and/or demographic information such as age and sex. Allen also discloses using spectral data to determine physiological states of human patients based on spectral variation. Allen 4:17-4:21. Spectrometers can be used to detect spectroscopic changes in skin color to determine physiological states in patients. This functionality can be used as a stress detector or as a lie detector. Allen discloses that stress in humans can cause changes in skin color, such as reddening, which can be detected spectroscopically. The changes in skin color are believed to result from changes in blood flow in the tissue as a result of stress. Allen 18:14-18:40.

U.S. Pat. No. 5,671,735 (MacFarlane et al.) discloses a method and apparatus for determining the condition of a test subject using a color measuring instrument to detect changes in a color factor indicative of a condition such as a disease, aging, etc. For example, a medical condition such as hyperbilirubinemia that affects skin color can be detected. Color factors such as Hunter b and L can be measured for the subject's skin. For predetermined ranges of one color factor, in particular L, changes in the other color factor, e.g. Hunter b, above predetermined levels are indicative of the medical condition. Sequential color readings can indicate the presence or absence of a condition based upon changes in the measured color factor, or lack of changes, over time.

When a medical condition affecting skin color is detected in a procedure like that described for hyperbilirubinemia, the measuring of skin color characteristics preferably continues at regular intervals until the symptomatic color characteristic abates sufficiently to indicate the individual's recovery from the medical condition. In the case of hyperbilirubinemia, phototherapy is administered once a sufficient change in Hunter b is observed to indicate the jaundice symptomatic of hyperbilirubinemia. Throughout the course of phototherapy, the Hunter b and L color characteristics are continually monitored until the jaundice has been eliminated and treatment can be discontinued. MacFarlane 2:66-3:9.

U.S. Pat. No. 7,483,733 (Shani et al.) discloses a non-invasive method and apparatus to detect and monitor medical shock. A color sensor is used to detect skin color changes from pink to white (when the skin is depressed to expel blood) and then back to pink (as blood returns to capillaries when pressure is removed) in the relevant skin area. The time required for the skin to return to a pink color (i.e. CFT—capillary filling time) is determined. Slow recovery to an oxygenated pink color is indicative of shock.

U.S. Patent Application Publication 2016/0073886 (Connor) discloses wearable spectroscopic sensors for measuring food consumption. Connor FIG. 19 shows an example of a wearable device for the arm with a plurality of close-fitting biometric sensors.

U.S. Pat. No. 5,564,417 (Chance '417) teaches a wearable tissue spectrophotometer for in vivo examination of tissue of a specific target region. Chance '417 1:12-1:14. The spectrophotometer includes a phase detector for measuring a phase shift between the introduced and detected light, a magnitude detector for determination of light attenuation in the examined tissue, and a processor adapted to calculate the photon migration pathlength and determine a physiological property of the examined tissue based on the pathlength and on the attenuation data.

Chance '417 describes a path length corrected oximeter that utilizes principles of continuous wave spectroscopy and phase modulation spectroscopy. The oximeter is a compact unit constructed to be worn by a subject on the body over long periods of activity. The oximeter is also suitable for tissue monitoring in critical care facilities, in operating rooms while undergoing surgery, or in trauma related situations. The oximeter is mounted on a body-conformable support structure placed on the skin. Chance 1:52-1:61.

U.S. Pat. No. 5,402,778 (Chance '778) discloses a system for examination of a relatively small volume of biological tissue of interest using visible or infra-red radiation and a spectrophotometer. The spectrophotometer is a continuous wave spectrophotometer, a phase modulation spectrophotometer, or a time-resolved spectrophotometer. Chance '778 Abstract. In one example a human finger is inserted into a hollow cylinder, and the optical properties of the finger are measured by a spectrophotometer.

U.S. Pat. No. 8,082,015 (Yodh et al.) discloses a device, system, and method for determining the characteristics of deep tissue. Blood flow rate characteristics are measured as a function of light fluctuations caused by the tissue, while the oxygenation characteristics are measured as a function of transmission of light through the tissue with respect to the wavelength of light. The tissue characteristics may be measured during times of varying levels of exercise intensity. Yodh Abstract. The invention relates to methods and apparatus for measuring the flow of blood and oxygenation characteristics using diffuse optical spectroscopy. Yodh paragraph 1:18-1:21. Generally, the measurement techniques derive tissue optical properties, for example, hemoglobin concentration and blood oxygen saturation from diffuse reflection spectroscopy (DRS) measurements, and blood flow from diffuse correlation spectroscopy (DCS) measurements. Yodh 5:20-5:24.

The above references are incorporated by reference, and should be considered as resources to support and assist implementation of the invention except to the extent that any references may provide definitions which directly conflict with definitions herein.

SUMMARY OF THE INVENTION

One aspect of the invention is a wearable color detector device for monitoring a patch of skin on a patient to detect and quantify color changes. "Color detector" refers to colorimeters, spectrophotometers, and equivalent devices capable of measuring at least red wavelength light. Color data may be saved on the device, or wirelessly transmitted to a remote storage module. The device includes a compact color measuring device (such as a spectrophotometric colorimeter) positioned on a patient for monitoring the skin surface. In one embodiment the device can be positioned on any area of a patient's skin, such as on a rear shoulder blade or scapula, typically in a clinical setting. In another embodiment, the device is provided on a wrist band or in a watch-like form which the patient can wear for longer periods, with the color detector positioned against skin on the patient's wrist. The color detector may communicate with a computing and/or storage device via Bluetooth, a USB cable connection, or other suitable means.

A light and color measuring device such as a spectrophotometer colorimeter apparatus is provided for tracking one or more physiological condition of a subject based on skin color changes. The color detector device may include an input for receiving light from the subject's skin, the light having a characteristic color that varies with at least one physiological condition of the subject, an output for outputting data containing information corresponding to the characteristic color of the light received at the input at selected times, and data processing means for converting the light received into the data. A mounting means may be provided for mounting the color detector to the subject at a location and in a manner for placing the input adjacent a selected area of the subject's skin. A data storage means is operatively connected to the output for storing the data for multiple selected times.

The color detector device can be used to monitor patient reactions to stimuli such as physical exercise or pharmaceuticals. Typically, quantitative L/a/b color scale measurements are taken over time on the same skin surface before, during, and after a treatment. The invention is not limited to a particular color quantification system. Skin color change and perfusion information is used to help tailor a treatment regimen for the patient, such as prescribing medication and exercise.

In one aspect, a color detector is placed on a patient's scapula while they perform a treadmill "stress test" under medical supervision. For example, the "Bruce Protocol" inclined treadmill stress test where speed and incline are incrementally increased over time. Vital signs and color detector measurements are taken every minute starting at time zero, in addition to recording subjective descriptions of how the patient feels. When the patient terminates the stress test the treadmill is stopped and the patient sits down, starting the recovery phase of the stress test. Vital signs and color detector measurements continue to be taken every minute starting at recovery time zero, such as for the first ten minutes of recovery.

In another aspect, a color detector is used to monitor a patient during a surgical or catheter procedure, or during a medical crisis such as in an ambulance or emergency room.

It has been determined that, broadly speaking, greater increases in skin color (especially an increase in "redness") and blood perfusion during the course of the stress test indicates better cardiovascular health. Less healthy individuals have relatively less color change for a given stimulus, or even a reduction in redness reflecting inadequate oxygenation. Healthy patients are able to achieve greater metabolic oxygen consumption during the test, which is accompanied and facilitated by widespread vascular dilation and increased redness in the skin (due to capillary dilation and increased blood flow). This color change is often too subtle to detect visually, and cannot be quantified visually. Therefore, methods using color detectors/light detectors such as spectrophotometric colorimeters to measure and quantify redness levels have been devised.

The instant invention includes methods, computer programs, devices, and arrangements for performing patient diagnosis, treatment, and monitoring using "dry runs" and/or "wet runs" as detailed herein. The invention includes methods and arrangements for detecting and quantifying skin perfusion and capillary dilation, changes in skin redness, and computer programs and colorimeters for use therewith. The invention further includes methods and arrangements for assessing the effects of exercise and pharmaceuticals.

The invention includes methods and related devices for determining a red shift for a patient during a stress test. For example, methods including:

(A) applying a wet run solution to a skin surface of the patient, the skin surface receiving wet run solution including a testing area of the skin surface; wherein the wet run solution includes, for example, acetylcholine. Additional efficacious wet run solutions have also been identified by the inventor, namely, bradykinin, adenosine, vasopressin, nitroglycerin, sildenafil, serotonin, and thrombin.

(B) positioning a color detector on the patient after the application of wet run solution, wherein the color detector (e.g. colorimeter or spectrophotometer) includes an input for receiving light, and wherein the input is positioned to receive light from the test area;

(C) making and saving a baseline color measurement of the testing area using the color detector, the baseline color measurement including a baseline skin redness level of the testing area;

(D) initiating an exercise protocol after the baseline color measurement, wherein the exercise protocol includes the patient engaging in physical exercise;

(E) making and saving a plurality of exercise color measurements of the testing area at different times during the exercise protocol, the exercise color measurements each including skin redness levels;

(F) ending the exercise protocol by the patient ending the physical exercise, such as because patient cannot continue or because a target heart rate has been achieved;

(G) after the exercise protocol ends, beginning a recovery phase, with the patient resting during the recovery phase such as by sitting or laying down;

(H) making and saving a plurality of recovery color measurements of the testing area at different times during the recovery phase, the recovery color measurements each including skin redness levels; and (I) calculating the red shift for the patient, the red shift being calculated by comparing the baseline skin redness level and one of a maximum skin redness level and a minimum skin redness level saved during the exercise protocol and recovery phase. For example, the maximum or minimum redness value from exercise color measurements and/or the recovery color measurements.

Preferred methods also include the exercise color measurements and the recovery color measurements being made at evenly spaced time intervals, the intervals being from 10 seconds and five minutes or from thirty seconds to three minutes.

The methods can also include providing an EKG machine, and collecting EKG data for the patient during at least the recovery phase.

The wet run solution may include acetylcholine and at least one of alcohol and water. The wet run solution may also or instead include acetylcholine and at least one of petroleum jelly and an oil. The wet run solution may also include bradykinin, adenosine, vasopressin, nitroglycerin, sildenafil, serotonin, and thrombin.

The exercise protocol may include the patient using at least one exercise machine selected from a treadmill, a stationary bicycle, an elliptical trainer, and an arm ergometer. The exercise protocol may be the Bruce protocol.

The method may include performing the steps described above before, and then again after, beginning a treatment including administration of a pharmaceutical or biologic medicine to assess the efficacy of the treatment. The second test may be at least one day, or a plurality or days, after initiation of the treatment. The treatment preferably included the patient receiving at least one dose of a pharmaceutical or biologic each day.

The skin surface monitored for the above methods may be a back, arm, wrist, or chest of the patient.

Preferred exercise protocols include increasing at least one of a speed and a resistance of the physical exercise one or more times, or repeatedly, at intervals, during the stress test.

The color detector may include an attachment element for reversibly attaching the color detector to a patient. The color detector can be physically attached to the patient with the attachment element such that the input for receiving light remains positioned at the testing area during the exercise protocol and/or the recovery phase.

The above methods may also include providing a second color detector including a respective second input for receiving light, and positioning the second color detector such that the second input is positioned to receive light from a different second test area, the second test area being a different part of the skin surface of the patient, where wet run solution is not applied to the second testing area. During performance of the steps (C)-(H), a plurality of dry run color measurements are made and saved using the second color detector including skin redness level at the dry second testing area. The dry run measurement made during performance of the steps (C)-(H), using the second color detector may include: (i) a dry run baseline color measurement taken before initiating the exercise protocol; (ii) a plurality of dry run exercise color measurements taken at different times during the exercise protocol; and (iii) a plurality of dry run recovery color measurements taken at different times during the recovery phase.

The invention also includes devices for determining a maximum red shift for a patient during a stress test according to any of the methods described herein. The device may include a processor and a memory, and may be operatively linkable to receive color measurement data from at least one color detector, the color measurement data including skin redness level data measured during a stress test with a patient. The device may also be configured to calculate the maximum red shift, using the color measurement data, by comparing the baseline skin redness level and the maximum or minimum skin redness level saved during the exercise protocol and recovery phase.

Additional arrangements of the invention include a color detector, and a console including a processor and a memory. Preferably the color detector is operatively linkable to the console such that the console can receive color measurement data from the color detector, the color measurement data including skin redness level data measured during a stress test with a patient. The same arrangements may be configured to calculate maximum or minimum red shift, using the color measurement data, by comparing the baseline skin redness level and the maximum or minimum skin redness level saved during an exercise protocol and recovery phase.

The invention also includes wearable arrangements for determining a skin redness for a patient during a stress test, and methods using wearable arrangements. Such arrangements may include a color detector, a mounting element, a processor, and a memory. Typically, the color detector is operatively linked to the processor and the memory for transmitting color measurement data including skin redness level data during the stress test. A mounting element for the color detector may be configured for reversibly attaching at least the color detector to a patient, and using one or more of a belt, a wrist band, an adhesive, hook-and-loop fasteners, an elastic band, and a buckle. Color detectors may be incorporated into or attached inside of a shirt or other item of clothing such that they can contact an appropriate skin area. Wet run solutions and chemicals can also be incorporated into the garment itself or a sorbent carrier positioned inside the garment in the vicinity of a wet run color detector.

Arrangements may be embodied as a color detector module including the color detector and a transmitter worn by the patient during exercise. Color measurement data may be wirelessly transmitted from the color detector module to a storage module including a memory during the stress test or exercise protocol where it is received and saved. The storage module may be a portable device such as a smart phone, or a remote system such a computer. Data may also be stored locally in other embodiments, or transmitted to a smart phone.

In some methods according to the invention the redness of the testing area of the skin surface declines during the exercise protocol. In such cases calculating the red shift may include comparing the baseline skin redness level with a minimum skin redness level measured during exercise or recovery, thereby determining a negative red shift value. The patient may be diagnosed as having unsatisfactory cardiovascular health based on the negative red shift value.

In other methods, the redness of the testing area of the skin surface increases by at least 20%, 30%, or 50% during the exercise protocol. Calculating the red shift then includes comparing the baseline skin redness level with the maximum redness level during exercise or recovery, thereby determining a positive red shift value of at least +10%, +30%, or +50% as applicable. The patient may be diagnosed as having satisfactory cardiovascular health in response to the positive red shift value of at least +10%, +30%, or +50%.

Devices configured for storing data and making such calculations and determinations are also contemplated.

The invention includes displaying on a display a graph plotting skin redness levels over a period of time. For example, a graph including a baseline color measurement, a plurality of exercise color measurements, and one or more recovery color measurements. Graphical displays may also compare wet run vs. dry run measurement for a patient over the course of a stress test.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Methods and devices according to this invention use one or more spectrophotometers, colorimeters, and/or other devices for detecting, measuring and quantifying color. Other devices which similarly measure color changes, especially changes in "redness" or a red/green color coordinate, are within the scope of the invention. Spectrophotometric colorimeters are a preferred device. Where the term "color detector" is used in this disclosure, it should be understood to also include a spectrophotometric colorimeter, colorimeter, spectrophotometer, as well as other equivalent devices, which will not be recited in each instance in the interests of brevity. Color measurements may be L/a/b values, the a value (red/green) only, R/G/B, or other known methods of color quantification. While many color monitoring devices detect and record a number of color parameters (e.g. L/a/b), preferred embodiments of this invention are primarily concerned with changes in the amount of red light reflected. Thus, devices and methods which only measure red or red/green spectrum light are also contemplated. One or more lights may be paired with a color measuring device.

Figure 1:
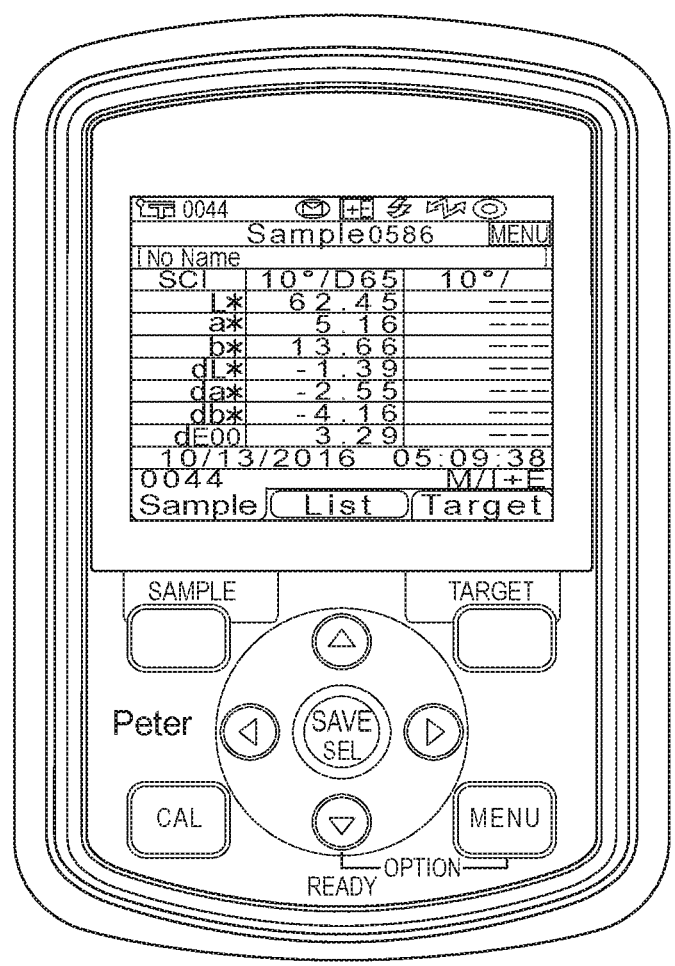
FIG. 1 is a spectrophotometer.

FIG. 1 is an example of a spectrophotometer, a type of color detector. L, a, and b color readings for the hand of an individual holding the colorimeter are visible on the display. Devices providing other outputs such as RGB (red/green/blue) can also be used.

Color detector measurements are preferably taken at the same location on the patient throughout the protocol. Less hairy and more easily accessible skin locations, such as the scapula, are preferred. The color detector device may be fixed on the patient for the duration of the procedure, or a color detector may be positioned at the measurement site for each reading and then removed. Color detector measurements are typically recorded and saved in a readable medium.

Preferred methods include "wet runs" where skin surface being monitored with a color detector is first treated with a wet run solution, as explained below. A preferred wet run solution includes acetylcholine as an active ingredient, in addition to water or other carriers. Additional efficacious wet run solutions include bradykinin, adenosine, vasopressin, nitroglycerin, sildenafil, serotonin, and thrombin.

"Dry runs" refer to protocols where the skin being monitored is not treated with a wet run solution, as detailed below, and also have applications.

Skin Color Change as Vascular Diagnostic Indicator

Work underlying this invention has found that change (or lack of change) in skin color in response to certain stimuli can be used to gauge vascular health. This is at least partially due to the fact that the same type of cells—endothelial cells—line substantially the entire vascular system, from the largest arteries down to the capillaries. The endothelium is a specific type of epithelium which lines the interior surface of blood vessels and lymphatic vessels, forming an interface between circulating blood (or lymph) and the rest of the circulatory vessel and body. The endothelium is a thin layer of simple squamous cells called endothelial cells. Endothelial cells in direct contact with the blood are called vascular endothelial cells. Endothelium making up the interior surfaces of the heart chambers is also known as endocardium. Identification of reduced functionality in capillary endothelium, as disclosed herein, can be used to identify vascular disease less invasively, and earlier in time, than known alternative methods.

In healthy individuals, physical exertion quickly leads to increased heart rate, blood flow, and blood vessel dilation. This facilitates increased oxygen delivery during exercise. Blood vessel dilation in this case is systemic, including both larger arteries and small capillaries such as those supplying blood and oxygen to the skin. Skin capillary dilation brings greater amounts of red oxygenated blood near the skin, which in turn increases the red color of the skin (aka "red shift", "alpha shift", or Δa) as compared to the resting state. This phenomenon has been observed across patients having various different skin tones. This color change is generally too subtle to detect visually, and cannot be quantified visually. Therefore, methods using light detectors such as spectrophotometric colorimeters to measure and quantify redness levels have been devised.

In healthy individuals, when exercise ends, heart rate, blood flow, and blood vessel dilation also return to resting levels relatively quickly. This, in turn, causes skin red color levels to return to resting color relatively quickly.

In patients with unhealthy circulatory systems, the dilation reaction from exercise is both reduced and delayed, reflecting a generally poor and slow physiological response to support physical exertion. The vascular dilation response (to help increase blood delivery) occurs more slowly, and to a lesser extent, than in healthy individuals. Thus the increase in blood flow to skin capillaries, and corresponding increase in red color, is reduced and delayed in unhealthy individuals (i.e. the peak Δa is low). In more severe cases, there may be little or no detectable increase in skin perfusion and redness. Patients having severe vascular disease (e.g. stenosis greater than 75%) may actually exhibit a negative red shift in response to exercise. The ability of the heart to pump sufficient blood to adequately perfuse the body for exercise is lower in significant part because of poor dilation in response to exercise throughout the vasculature, including in the capillaries. When exercise ends, unhealthy patients also take longer to return to resting vessel dilation state and red levels. This reflects a greater need to compensate for oxygen deficits created during exercise, reduced ability to compensate for those oxygen deficits, and generally slower reactions rates.

In a healthy individual, exercise triggers a significant positive red shift (i.e. increase in skin redness) from the resting baseline which can be represented as a curve on a graph. See FIG. 1. The slope or steepness of this increase and decrease will vary, but the general up and down curve is typical among healthy individuals. This holds true using both wet and dry run methods, though the degree or red shift is usually greater with wet run methods in healthy individuals. Steeper inclines and a shorter time to peak positive red shift are correlated with better cardiovascular health. This is because steep inclines indicate a rapid body response to exercise to increase blood perfusion, and distribute more blood and oxygen when it is needed.

FIGS. 2-5 represent typical and idealized graphs of red shift over time during stress tests to illustrate principles identified over the course of numerous procedures with individual patients. Graphs of individual patent red levels, recorded periodically (e.g. every minute) may be less smooth and, in some cases, may deviate from the idealized-but-typical examples which are provided for illustrative simplicity.

Figure 2:
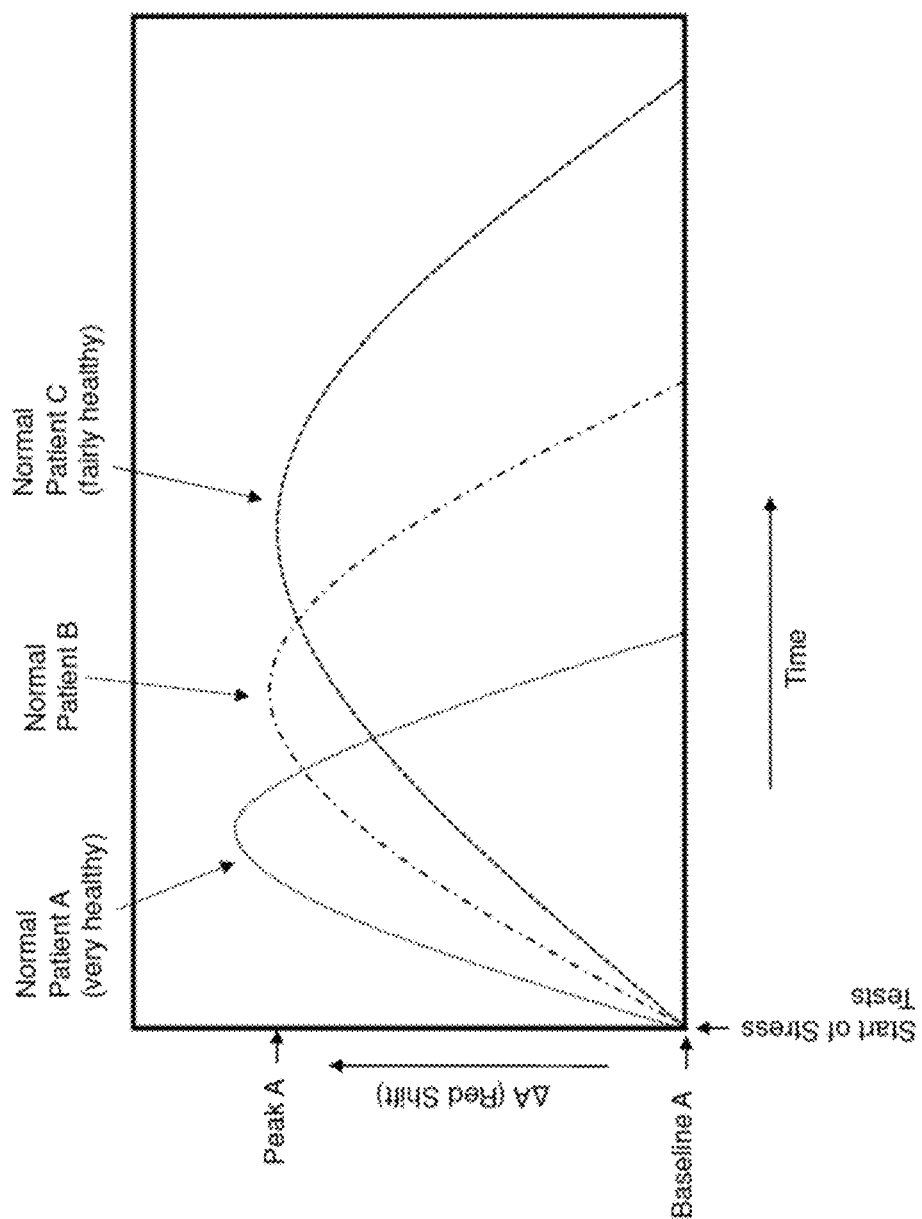
FIG. 2 is an illustrative graph of red shift over the course of a stress test for three different normal patients.

FIG. 2 shows illustrative graphs of red shift over time for three typical idealized "normal" patients undergoing colorimetric monitoring during exercise. Units are not specified in these illustrative graphs. The start of exercising is indicated by the left origin of each curve. Exercise continues until peak exercise, indicated by the respective points at the top of each curve. Peak exercise may be determined based on reaching a predicted maximum heart rate and is frequently (but not always) maximum positive red shift. After this point recovery begins and, typically, skin color begins to return to baseline at the right end of each curve. All three patients in FIG. 1 are considered normal and very healthy to reasonably healthy because they have a substantial positive red shift (indicating increased perfusion) during the course of the activity. Patient A is in the best condition of the three because they reach peak red shift (indicating elevated perfusion) the most quickly. Patients B and C are the second and third best cardiovascular health, in that order, based on the time required to reach peak red shift.

Figure 3:
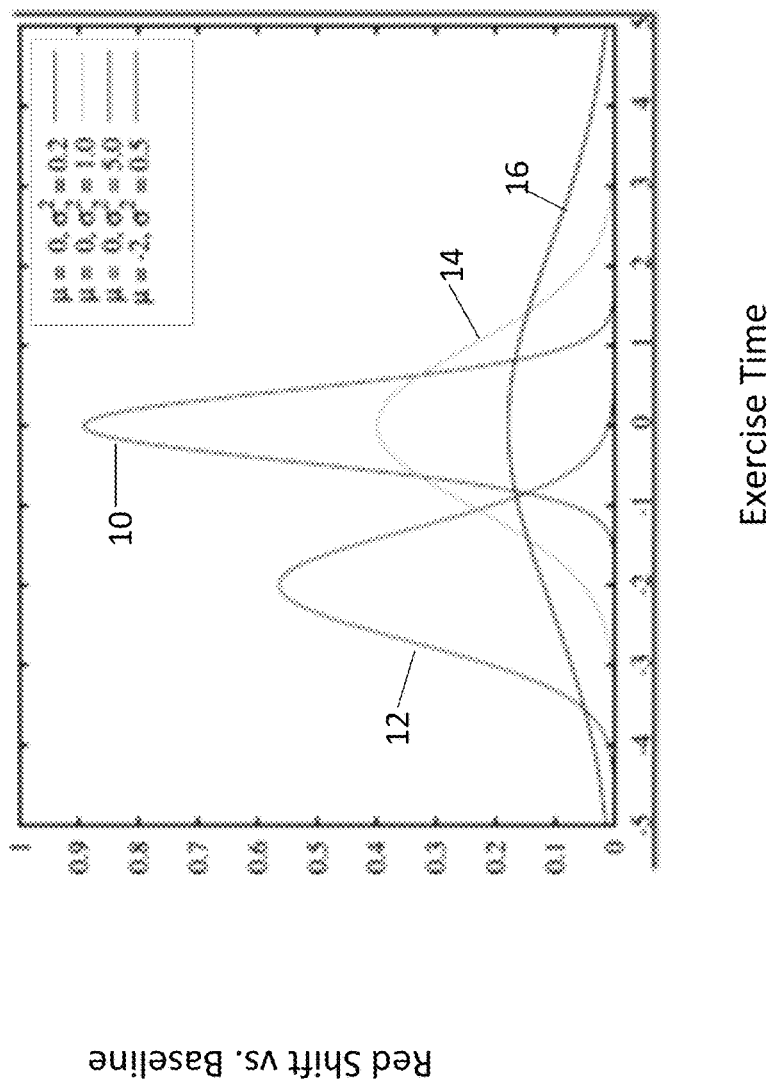
FIG. 3 is an illustrative graph of red shift over the course of a stress test comparing healthy and unhealthy patients.

FIG. 3 shows illustrative graphs of red shift over time as four patients in varying states of vascular health perform an exercise routine. Time and red shift units are arbitrary, but all curves are on the same scale for comparison purposes. The patient represented by the tallest curve 10 is in the best cardiovascular health, exhibiting fast and substantial red shift during exercise. At the other extreme, the patient represented by curve 16 has the poorest vascular health, managing only a small and slow positive red shift during exercise. This indicates that they have only weak ability to increase blood and oxygen flow during exercise, and that what response they are able to achieve is slow. The patients represented by curves 12 and 14 are the second and third healthiest, respectively, based on the size of their red shift peaks and times required to achieve peak perfusion. Healthier patients also usually recover (i.e. return to baseline redness and perfusion) more quickly.

Figure 4:
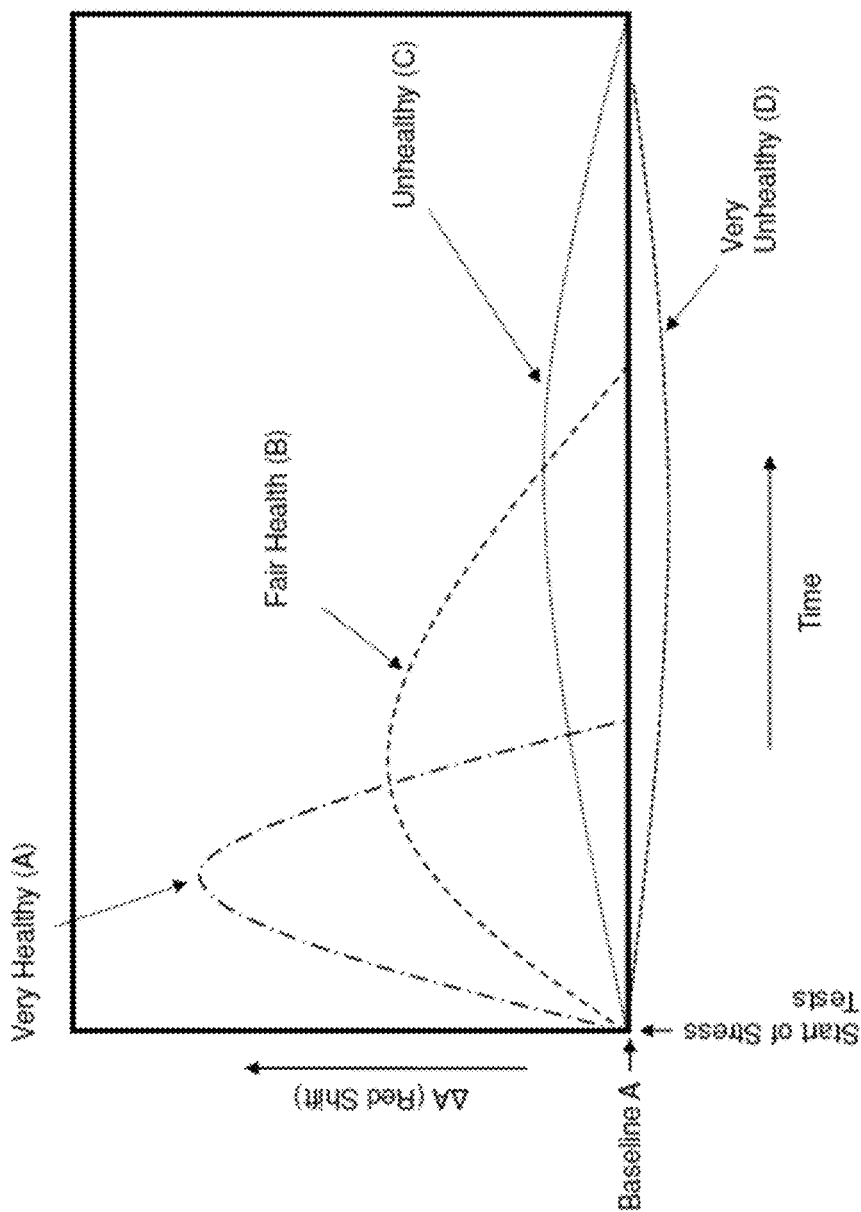
FIG. 4 is a second illustrative graph of red shift over the course of a stress test comparing healthy and unhealthy patients.
Figure 5:
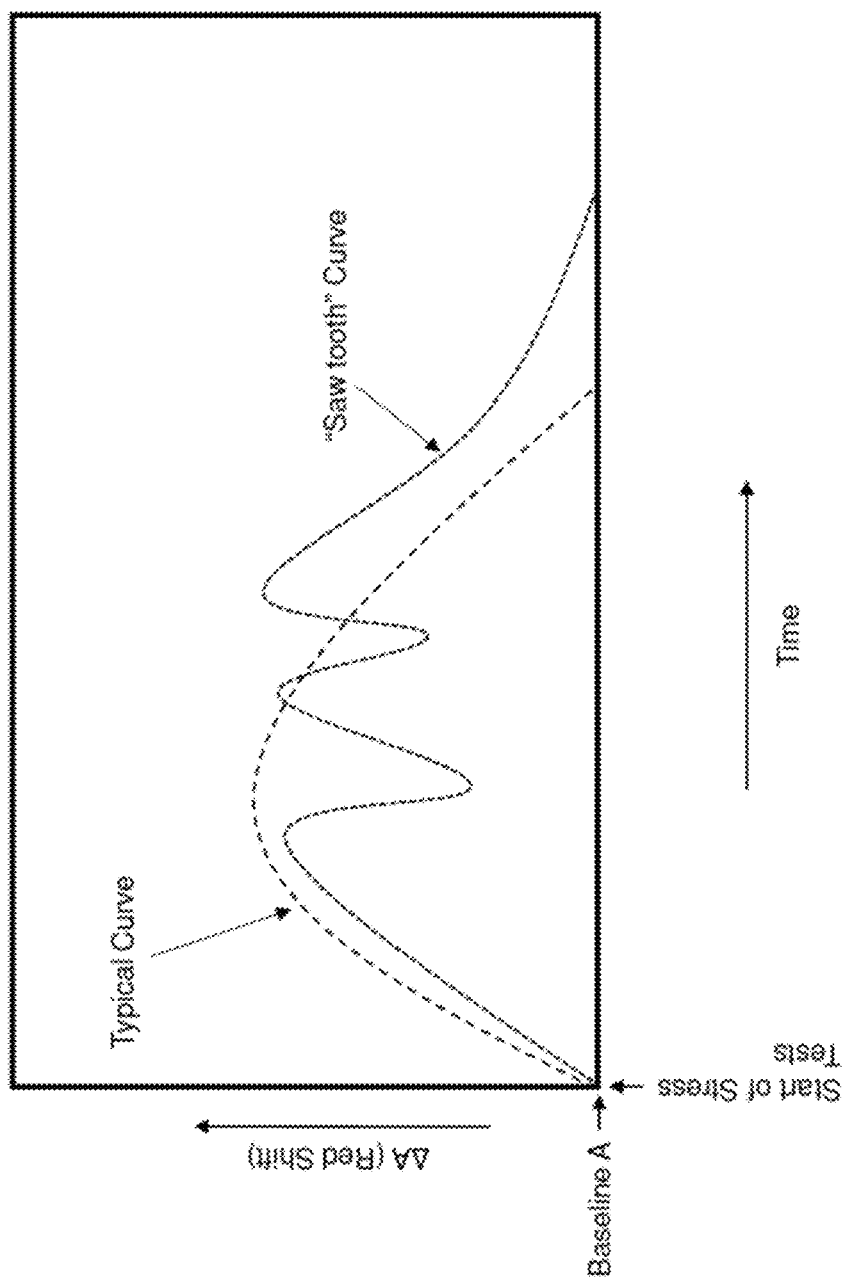
FIG. 5 is an illustrative graph comparing normal and sawtooth red shift curves.

FIG. 4 illustrates similar principles as FIG. 3, comparing stress tests (e.g. wet run) by four patients in varying states of cardiovascular health. Patient A is healthiest, having the greatest red shift which is also achieved quickly, followed by rapid recovery and return to baseline. Patient D is in very poor cardiovascular health, and actually has a negative red shift during stress test, indicating a pallid color and inadequate perfusion.

"Red shift" refers to change in skin redness. Different individuals have different complexions and different baseline/resting red levels in their skin, but red shift can be quantified in relative terms. For example, in terms of a % change in the red (A) value the L*a*b* color space or Hunter L/a/b color space, although other red quantification systems may be applied similarly. Typical stress test peak red shift values indicative of good cardiovascular health would be +10%-+100%, +30%-+70%, +10% or more, or +30% or more compared to resting. Stress test peak red shift (or in the case of negative red shift, minimum) values indicative of poor cardiovascular health include +10% or less (including negative shifts), 0% or less (i.e. no change or negative red shift), +10% to −100%, or 0% to −100%. Negative red shift values may be descriptive of a patient who exhibits a "pallid" or "white" appearance in response to exercise, depending on normal complexion.

A "sawtooth" red shift curve also indicates cardiovascular illness. See FIG. 5. A sawtooth curve is characterized by having multiple pronounced peaks over the course of a single exercise session/single stress test. For example, a stress test where red levels go up, down again by at least 25% or at least 33%, and back up again one or more times during the course of a continuous exercise session. This is evidence of an unsteady, vacillating vascular response to stress. Healthy patients may show slight up-down-up activity as a result of normal variation or reaction lag, reading margin of error, etc. and still be considered normal. "Sawtooth" patterns refer to curves with highly pronounced up-down-up vacillation, e.g. including redness increases, then declines of at least 25% or at least 33%, followed by further increases of at least 25% or at least 33%.

In particular, sawtooth red shift patters have been associated with obstructive artery disease during the work supporting this invention. Sawtooth red shift patterns during a stress test are indicative that further diagnostic steps for obstructive coronary artery disease, and potentially recommend treatments such as aspirin, other medication, balloon angioplaty, stent placement, or coronary bypass surgery as needed. In contrast, "smooth" curves having low or negative red shifts but only a single peak are associated with non-obstructive coronary artery disease, such as tachycardia or malignant ventricular arrhythmias.

This invention includes methods of diagnosing cardiovascular health by measuring skin red shift during exercise, most preferably using wet run methods during a stress test, and comparing results with these typical values. The invention also includes arrangements including color detectors, computer programs, and processors configured for use with such methods. The invention also includes kits which include color detectors and skin applications for performing wet run methods.

Red shift based methods according to this invention can be used to identify cardiovascular improvement (when present) due to medication, exercise regimens, open heart surgery, catheter surgery, stenting, new diets, or other procedures intended to improve vascular health. The goal, broadly, is that the patient has a response (e.g. a red shift curve per above) corresponding to a "healthier" person after the treatment.

The inventor's work has identified previously unknown differences in the reactions of healthy and unhealthy individuals to acetylcholine and other vasodilative substances when applied to the skin. Acetylcholine creates a significant and detectable capillary dilation and positive red shift (due to increased blood flow) when applied to the skin of healthy individuals. Individuals with weaker circulatory systems, in contrast, have weaker or no dilation and red shift response to topical acetylcholine. Additional efficacious wet run solutions include bradykinin, adenosine, vasopressin, nitroglycerin, sildenafil, serotonin, and thrombin.

As stated above, and without being bound by theory, acetylcholine is believed to dilate normal blood vessels by promoting the release of a vasorelaxant substance from the endothelium (endothelium-derived relaxing factor). *Paradoxical Vasoconstriction Induced by Acetylcholine in Atherosclerotic Coronary Arteries*, P L Ludmer et al., N Engl J Med. 1986 Oct. 23; 315(17):1046-51. This study reported that acetylcholine caused a dose-dependent dilation in coronary arteries. It also reported dose-dependant constriction in coronary arteries with advanced stenosis. Five of six vessels with minimal disease also constricted in response to acetylcholine.

Work leading to the instant invention identified previously unknown parallel responses to acetylcholine in healthy and unhealthy vasculature beyond the coronary artery, most notably in skin capillaries. Further, and importantly for the instant invention, correlation has been identified between the dilation reactions (or lack thereof) of large arteries and of capillaries within individual patients. This is understood to be at least partly due to the fact that large arteries and narrow capillaries are all lined by endothelial cells which (1) have similar reactions to many stimuli, and which (2) are similarly limited throughout the circulatory systems in individuals with vascular disease. Healthier endothelium is believed to be more reactive to exercise and acetylcholine (for example) than unhealthy endothelium regardless of where in the body it is located. In essence what occurs in capillaries near the skin (or mucous membrane) is also occurring in the endothelium in the heart.

Thus, it has been determined that vascular and endothelial health for a patient as a whole can be gauged by measuring capillary dilation in the skin based on subtle color changes. Novel methods and apparatus for measuring capillary dilation in the skin, and for related diagnoses and treatments, are discussed elsewhere in this disclosure.

As stated above, one available quantitative color system is the L*a*b* color space or Hunter L/a/b color space, which can be visualized as a rectangular 3D coordinate system. L indicates lightness, a is the red/green coordinate, and b is the yellow/blue coordinate. L can have a value from 0 (black) to 100 (perfect reflection). The a and b axes have no numerical limits. Coordinate a is positive when red, and negative when green. Positive b is yellow, and negative b is blue. Colors can be described numerically using numerical values for L, a, and b. Differences between two colors can be quantified for each of the individual L/a/b values ($\Delta L$, $\Delta a$, $\Delta b$). Overall differences between two colors can be derived numerically based on the three $\Delta$ values.

Defined by the Commission Internationale de l'Eclairage (CIE), the L, a, b color space was modeled after a color-opponent theory. As shown below, L indicates lightness, a is the red/green coordinate, and b is the yellow/blue coordinate. Deltas for L ($\Delta L$), a ($\Delta a$) and b ($\Delta b$) may be positive (+) or negative (−).

$\mu$=drug applied before colorimeter and/or spectrophotometer measurements.

L1, a1, b1=Initial measurement.

L2, a2, b2=Measurement with $\mu$ applied.

$L2-L1=\Delta L\mu$ ($L2$ minus $L1$)=change in lightness and darkness(+=lighter,−=darker)

$a2-a1=\Delta a\mu$ ($a2$ minus $a1$)=change in red and green(+=redder,−=greener)

$b2-b1=\Delta b\mu$ ($b2$ minus $b1$)=change in yellow and blue(+=yellower,−=bluer)

To assess the degree of response variance as a baseline for the patient percentage values are obtained as follows:

$$\frac{\Delta L\mu}{L1} \times 100 = \% \ \Delta L\mu = \text{of change in } L$$

$$\frac{\Delta b\mu}{b1} \times 100 = \% \ \Delta b\mu = \text{of change in } b$$

$$\frac{\Delta a\mu}{a1} \times 100 = \% \ \Delta a\mu = \text{of change in } a$$

Drug $\delta$ given to patient at 5 half-lives to reach a steady state level in the body. (Reference must be made to medicine literature to confirm half-life established for each ($\delta$) drug.)

$\beta L1$, $\beta a1$, $\beta b1$=initial measurement after $\delta$ is administered.

$\beta L2$, $\beta a2$, $\beta b2$=Measurement after $\delta$ is administered with $\mu$ applied.

$\beta L2-\beta L1=\Delta\beta L\mu$ $\beta a2-\beta a1=\Delta\beta a\mu$ $\beta b2-\beta b1=\Delta\beta b\mu$ When $\Delta\mu$ is a positive result that is a healthy response, no change or negative result is unhealthy response. There are exceptions to this rule, by design, with heart failure medications their efficacy may be verified by the negative resultant.

To determine the total color variance of all three coordinates, with the treatments ($\delta$) drug given the following formula is used:

$$\frac{\Delta \beta L \mu}{\beta L1} - \frac{\Delta L \mu}{L1} \times 100 =$$

% $\Delta \beta L \mu$ = percent of change in $L$ with $\sigma$ administered $$\frac{\Delta \beta b \mu}{\beta b1} - \frac{\Delta b \mu}{b1} \times 100 =$$

% $\Delta \beta b \mu$ = percent change in $b$ with $\sigma$ administered $$\frac{\Delta \beta a \mu}{\beta a1} - \frac{\Delta a \mu}{a1} \times 100 = \% \, \Delta \beta a \mu =$$

percent change in $a$ with $\sigma$ administered

These calculations evidence the difference in the vascular endothelium and to the microvasculature after the medication "drug δ" given. A minimum of 5 half lives administered doses is needed to assess the minimum change that could take effect or until the pharmacokinetic and pharmacodynamic steady state is achieved for each particular drug (i.e. Crestor, Lipitor). Assessment of percentage change should be documented at regular intervals (weekly or daily) and verified on continuous basis by the healthcare provider. These findings objectively verify improvement or lack thereof provided by the drug tested.

The endothelium responds instantaneously to the effects of drug μ, so the benefit gained by drug (δ) will be seen when the equation results are compared to the patients baseline results. In healthy subjects, the effects of the medication drug δ are expressed, there will be increased blood flow, which is able to be measured and calculated using the equations above.

The health care provider will evaluate if the patient is taking a beneficial medication if the calculation results show increase equal to or greater than 10%. If the result of 10% or more are not achieved then the patient, along with health care providers, must consider the option of changing the medication to a different medication so that they will be able to achieve the desired effect of a greater red-shift change based on the readings of be a, b, L and spectrophotometric measurement after they are calculated before and after the drug "μ" is given. The drug μ allows for the assessment of the effects of the drug δ because as the microvascular endothelium approaches a healthier homeostasis. It will cause further dilation of the capillaries and a further increase in blood flow and a change in the color of the a, b, L towards a redder shift or equal to or greater than 10%.

With this process, it is possible to ascertain which medication the patient has a better direct response to and then compare the effects of one medication to another in the same class that was not previously possible (e.g. the difference between Zocor® (simvastatin) and Lipitor® (atorvastatin calcium). The specificity provided by this process is unique and much needed for patients afflicted by chronic illness/es. This process clearly identifies the benefits of a class of drug and dosage for any particular patient. This process is also promising for patients which may require multiple interacting drug therapies to avoid overprescribing and overdosing medications which are not beneficial.

The same method can be implemented for different classes of medications such as hypertensive medications, anti-arrhythmic medications, chemotherapeutic medications, diabetic medications, etc. All medications have an impact in the micro vascular circulation of the endothelium. The health of the endothelium will always be able to be assessed and calculated objectively with the colorimeter and/or the spectrophotometer after the drug "μ" is applied.

The measurements will have to be taken multiple times during the day and calculated for the individual that is being assessed and followed progressively while on this medication while the patient is both in a seated relaxed position as well as the patient needing to be physically mobile and trying to have an increased and chronotropic competence of the myocardium. Different pathophysiological effects occur while the patient increases their heart rate from a baseline steady state condition. The path of this physiological mechanism is able to be calculated and assessed objectively with the various medication described above and by the implementation of the methods set forth herein.

Stress Test Measuring a, b, L:

In order to evaluate the augmentation of the myocardium after an increase in the chronotropic response to the heart by physical activity and to increase the ionotropic augmentation of the myocardium the person will walk on the treadmill or can perform physical activities such as cycling or be chemically challenged with different pressors e.g. dobutamine to increase the functioning of the heart described above.

Therefore, the evaluation of the augmentation of the heart with increased chronotropic competence and ionotropic augmentation will be directly proportional to the $\Delta$ seen in the a value of the colorimeter as compared to baseline in a normal function of the myocardial augmentation. It is within the scope of the invention for there also be a proportional direct or indirect $\Delta$ seen in the b, L of the colorimeter and spectrophotometer as compared to baseline in a normal function of the myocardial augmentation.

Figure 17:
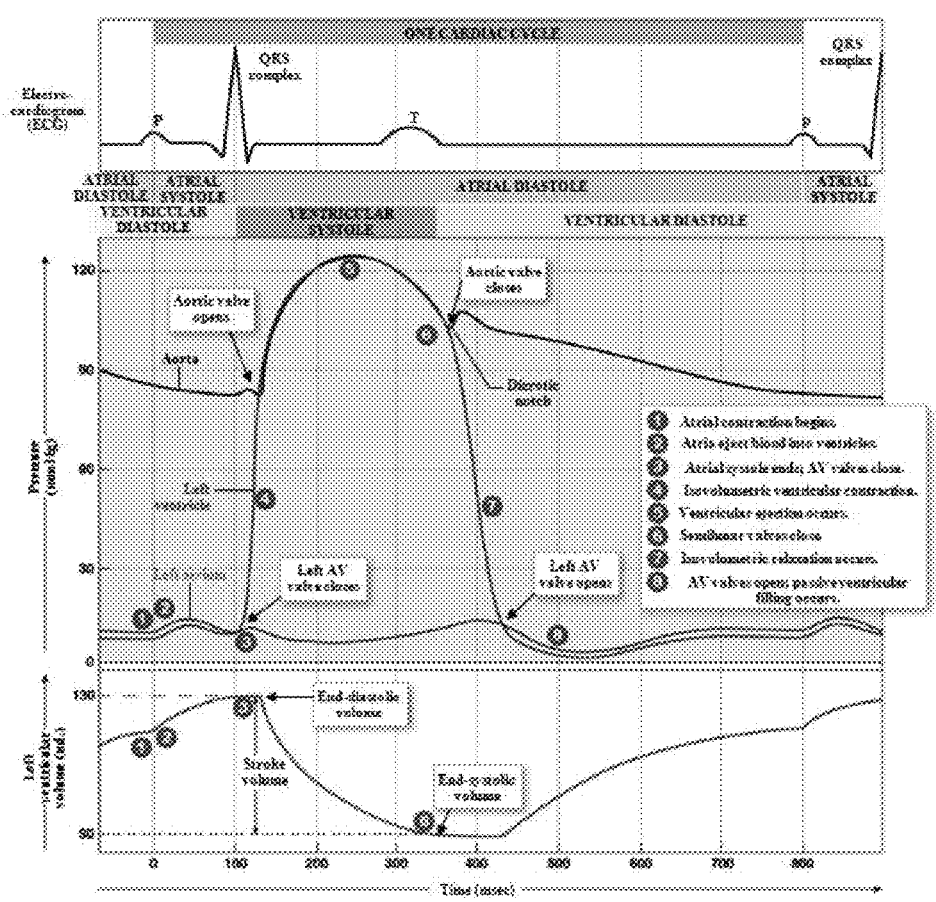
FIG. 17 depicts a graph depicting pressure and volume relationships in the cardiac cycle.

The acquisition of the optimum time to take the measurement of the a, b, L will be 100 to 200 milliseconds after the peak "R" wave of the QRS complex. This will allow to achieve the optimum flow of the cardiovascular system and will achieve the capability of measuring the maximum flow to the peripheral circulation where the measurement of a, b, L can be taken easily i.e on the arm, hand, thigh, leg, foot, head, neck, chest abdomen. This 100 to 200 millisecond time will assure the peak capability of measuring the variables described above this can be achieved by synchronizing the QRS occurrence through an electrode on the skin that is synchronized to the measurement of the picture acquisition that measures the a, b, L. This process can be applied to all measurements for stress testing and evaluation of drug testing. This will allow for consistency and optimum measurement of the a, b, L (See FIG. 17).

The evaluation of a flat effect or a decrease in the a colorimeter value during a positive chronotropic response will have an implication of an altered augmentation of the myocardium. This inappropriate ionotropic augmentation demonstrates an ischemic or electrical abnormality of the myocardium needing further diagnostic evaluation and intervention. The difference of the $\Delta$ in a negative value will be proportional to the decreased level that the augmented myocardium is demonstrating based on the "a" color (The larger the negative value the more the ischemic or electrical abnormality burden that is present in the myocardium).

During a positive chronotropic response resulting in a positive ionotropic augmentation the "a" should increase. This signifies that with the placement of the p, there should be more blood available to a healthy microcirculation because p will dilate in a healthy microvascular state.

During a positive chronotropic response resulting in a flat or negative ionotropic augmentation the "a" should stay the same or decrease. This signifies that with the placement of the μ, there should be less blood available to a diseased microcirculation because p will constrict endothelium in a diseased micro vascular state:

$$L2^{ST} - L1^{ST} = \Delta L^{ST}$$

$$a2^{ST} - a1^{ST} = \Delta a^{ST}$$

$$b2^{ST} - b1^{ST} = \Delta b^{ST}$$

$L1\mu^{ST}, a1\mu^{ST}, b1\mu^{ST}$ = pretest measurements of $a,b,L$ after $\mu$ is applied $L2\mu^{ST}, a2\mu^{ST}, b2\mu^{ST}$ = post stress test measurement of $a,b,L$ at end of stress test after $\mu$ is applied $L2\mu^{ST} - L1\mu^{ST} = \Delta L\mu^{ST}$ ($L2\mu$ minus $L1\mu$) = change in lightness and darkness(+=lighter,−=darker)

$a2\mu^{ST} - a1\mu^{ST}$ 32 $\Delta a\mu^{ST}$ ($a2\mu$ minus $a1\mu$) = change in red and green(+=redder,−=greener)

$b2\mu^{ST} - b1\mu^{ST} = \Delta b\mu^{ST}$ ($b2\mu$ minus $b1\mu$) = change in yellow and blue(+=yellower,−=bluer)

To assess the degree of response variance as a baseline for the patient percentage values are obtained as follows:

$$\frac{\Delta L\mu^{ST}}{L1\mu} \times 100 = \% \Delta L\mu^{ST} = \text{percent of change in } L \text{ post stress test}$$

$$\frac{\Delta b\mu^{ST}}{b1\mu} \times 100 = \% \Delta b\mu^{ST} = \text{percent change in } b \text{ post stress test}$$

$$\frac{\Delta a\mu^{ST}}{a1\mu} \times 100 = \% \Delta a\mu^{ST} = \text{percent change in } a \text{ post stress test}$$

$\beta L1^{ST}$, $\beta a1$, $\beta b1$ = Initial measurement after $\delta$ is administered.

$\beta L2^{ST}$, $\beta a2^{ST}$, $\beta b2^{ST}$ = Measurement after $\delta$ is administered with $\mu$ applied.

$$\beta L2^{ST} - \beta L1^{ST} = \Delta\beta L\mu^{ST}$$

$$\beta a2^{ST} - \beta a1^{ST} = \Delta\beta a\mu^{ST}$$

$$\beta b2^{ST} - \beta b1^{ST} = \Delta\beta b\mu^{ST}$$

$$\frac{\Delta\beta L\mu^{ST}}{\beta L1\mu} \times 100 = \% \Delta\beta L\mu^{ST} = \text{percent of change in } L$$

$$\frac{\Delta\beta b\mu^{ST}}{\beta b1\mu} \times 100 = \% \Delta\beta b\mu^{ST} = \text{percent change in } b$$

$$\frac{\Delta\beta a\mu^{ST}}{\beta a1\mu} \times 100 = \% \Delta\beta a\mu^{ST} = \text{percent change in } a$$

$(\%\Delta\beta L\mu^{ST} + \% \Delta\beta b^{ST} + \Delta\beta a\mu^{ST}) - (\%\Delta L\mu^{ST} + \% \Delta b\mu^{ST} + \%\Delta a\mu^{ST}) = \Delta\Sigma^{ST}$ Calculated augmentation of myocardium during stress testing.

A positive increased value is equal to a change in the percentage difference of an appropriate response to a stress test. That means there is an appropriate positive ionotropic effect of the ejection fraction of the heart with an appropriate increase in wall motion augmentation of the myocardium A flat or negative response of a decreased value in the percentage difference of the response to a stress test means there is no appropriate ionotropic effect of the ejection fraction of the heart. This may signify a poor response or poor outcome indicating inappropriate augmentation of the myocardium during exercise which necessitates further medical inquiry and testing.

A positive $\Delta$ (increased) value is equal to a change in the percentage difference of an appropriate response to a stress test. That means there is an appropriate positive ionotropic effect of the ejection fraction of the heart with an appropriate increase in wall motion augmentation of the myocardium A flat or negative $\Delta$ response of a decreased value in the percentage difference of the response to a stress test means there is no appropriate ionotropic effect of the ejection fraction of the heart. This may signify a poor response or poor outcome indicating inappropriate augmentation of the myocardium during exercise which necessitates further medical inquiry and testing.

Other Methods in Evaluating the Effects of the Microvasculature Circulation Before Application of "$\mu$":

The baseline homeostasis of the patient is given $\delta$. Afterwards, the flow to the microvascular circulation in the endothelium should change in the endothelium. By applying $\mu$ a catalyst, the flow to the microvascular circulation of the endothelium will be augmented significantly causing more color shifts that will be 10% greater or less, after the application of the "$\mu$" catalyst. In addition to the method described above, the specificity and sensitivity of the measurements obtained can be increased by adding this additional step. Before the application of $\mu$, the patient can simply increase the heart rate by walking a few steps or if the patient cannot walk because they are bed bound they can increase their heart rate by physically exerting their arms by performing constant circular rotations in a seated or bed bound position. Then, the p can be applied and the colorimetric and spectrophotometric calculations can be measured. This then can allow the evaluation and change in treatment strategy to the patient by altering the dosage of the $\delta$ that was being given or changing the $\delta$ to a different one in the patient's drug regimen. The evaluation of diabetic level and sugar level and hemoglobin A-1 C level based on daily requirements and the attachment of a device according to the present invention. As the devices attached to the subject, evaluation of the microcirculation that is completely dependent on the hemoglobin A-1 C will be able to be monitored within the patient closely as the color will achieve a biometric steady state level that will demonstrate A consistent pattern based on the patient's hemoglobin A-1 C that is individually processed through the biometric analysis of the a, b, L.

Evaluation of Anti-Arrhythmic's with Loading and Evaluation Monitoring of QT Prolongation:

Anti-arrhythmic medications can be further clarified and have their effects evaluated consistently with the colorimeter/spectrophotometer after drug "$\mu$" is applied and then measured and calculated with equations above because the effects after administering different antiarrhythmics will cause a change in cardiac augmentation of the left ventricular function which in turn will affect the micro vascular circulation flow. The micro vascular circulation flow should increase because of a better chronotropic and ionotropic effect of the myocardium that is directly caused because of the administration of the anti-arrhythmic's.

Using the above practices and calculations described in measuring the microvascular calculation, the inventor has been able to calculate the beneficial effects of the anti-arrhythmic's to the microcirculation indirectly. If there is better myocardial wall motion augmentation there will be better circulation and hence better blood flow with increased micro vascular flow causing a change in the response to a, b & L. This will be measured and calculated and if it is equal to or greater than 10%, then the anti-arrhythmic results in a better augmentation of blood flow that is measured with the colorimeter/spectrophotometer after drug "µ" is applied and then measured. If the value is less than 10% then this may signify no benefit from the anti-arrhythmic drug. The measurement will have to be taken multiple times during the day and calculated for the individual that is being assessed and followed progressively while on this medication while the patient is both in a seated relaxed position as well as the patient needing to be physically mobile and trying to have an increased and chronotropic competence of the myocardium (increased heart rate). Different pathophysiological effects occur when the patient increases their heart rate from a baseline steady state condition. This path of physiological mechanism is able to be calculated and assessed objectively with the various medication described above and the implementation of the methods set forth herein. When the heart rate is stabilized by the anti-arrhythmic drug the heart rate will be more consistent and uniform. Therefore, the flow to the microcirculation will be also more uniform and follow baseline homeostatic characteristics signifying that the wall motion augmentation of the heart and the chronotropic effect is back in normal sinus rhythm. When Premature ventricular Contraction (PVC) occurs, or Bigeminy (two PVC alternating), or Trigeminy (three PVC alternating) the contracting myocardium is not able to appropriately circulate the blood flow appropriately throughout the circulatory system because of the improper contraction of the heart ventricles. This will alter the myocardial flow to the microcirculation. The above-mentioned practices and measurements with the a, b, L will allow to be appropriately measure and calculate after the application of the "µ". The diagnosis of the ventricular arrhythmia will then be able to be diagnosed because of the change in the microvascular circulation blood flow altering the a, b, L. After the administration of the anti-arrhythmic drug e.g. metoprolol or diltiazem, the measurement and quantification of the flow to the microvascular circulation will become more uniform and consistent signifying a return to a baseline normal sinus rhythm. If the administration of the anti-arrhythmic drug did not have a desired effect with the measurement and calculation of the a, b, L, when "µ" is applied then the dosage or anti arrhythmic drug or both need to be changed to therapeutically establish a normal sinus rhythm baseline again for the patient.

Anticoagulation Effects of Blood Thinners

Patients require treatment with blood thinners for various conditions such as atrial fibrillation, embolisms in the lungs, and or thrombosis in the legs experience continuous clotting and thrombolysis in the endovascular endothelium. This constant cascade of events (clotting and unclotting) continue to repeatedly occur in the micro environment of the endothelium. The flow of blood through this microscopic circulation will be affected by the addition of an anti-clotting medication (i.e. Coumadin® (warfarin), Pradaxa® (dabigatran), Xarelto® (rivaroxaban), Eliquis® (apixaban), Plavix® (clopidegrel), Brilinta® (ticagrelor), Kengreal® (calgrelor), Effient® (prasugel), aspirin, Pletaal® (cilostazol)) the process of these anticoagulation medications will decrease the ability of the intrinsic and extrinsic coagulation pathway and platelet clump formation from occurring. Therefore, the flow would be increased because of the addition of the aforementioned medications and the a, b, L shift will be greater than the baseline after the application of "m" because of the medications that were applied and taken. Therefore, the status of the anti-coagulation and the effectiveness of the anti-coagulation system will be ascertained based on the medication class and dosage that is given. This will allow the healthcare provider to know the medications' effectiveness and if a dose adjustment needs to be made or a different medication may need to be implemented at this time because the effectiveness of the administered medication has not achieved the desired effect. this will be used along with current standards that are implemented at this time to assess contrast and compare the effectiveness of the medication that has been taken by the patient.

Heart Failure Medications

Heart Failure is a pathophysiological state where the myocardial augmentation is not able to be achieved appropriately for baseline steady-state conditions. Various medications are administered to specifically decrease the chronotropic and lonotropic effects of the heart. When different types of heart medications are administered in heart Failure, the healthcare provider is trying to slow down and decrease the strenuous activity of the heart un-natural and inappropriate augmentation because of the heart failure. The medications administered will decrease the flow to the cardiovascular microcirculation of the endothelium. In a resting position without exertion the a, b, L measurements and calculations may be lower after the implementation of the medication drug "δ" given. However, after five drug "δ" Half-lives or more, The flow to the microvascular circulation will improve after the patient has a minimum increase in their chronotropic and ionotropic effect of their heart which can easily be performed by the simple act of walking. Then the measurement of the colorimeter/spectrophotometer calculation of the measurement after drug "µ" is administered will demonstrate an increase of equal to or greater than 10% measurement described above. This will, therefore, allow the patient, with his/her healthcare provider, to determine which class of medicines or which types of medicines for anti-heart failure or more beneficial to the patient based on the measurement that is obtained after drug "µ" is applied and calculated.

The procedure described above will allow for an objective evaluation of which drugs have a meritorious benefit to the patient for the treatment of their heart failure and will allow for a better and improved recovery. The higher the percentage difference of equal to or greater than 10% the better the drug. Therefore, the patient will be able to determine which drugs meritoriously benefit their prognosis i.e. ace inhibitor versus angiotensin receptor blocker. The above-mentioned process will be able to ascertain as well as which medicine in the same class of drugs "δ" is also better for the treatment modality of the patient i.e. Monopril® (fosinopril) versus ramipril. The above modality will be able to better implement treatment strategies based on the color the metric and spectrophotometric calculation after drug "µ" is applied and measurement of the a, b, L is calculated.

The measurement will have to be taken multiple times during the day and calculated for the individual that is being assessed and followed progressively while on this medication while the patient is physically mobile while performing either walking or circular arm movements as described above and try to have an increased chronotropic and ionotropic competence of the myocardium. Different pathophysiological effects occur while the patient increases their heart rate from a baseline steady state condition. This path of physiological mechanism is able to be calculated and assessed objectively with the various medications drug "δ" described above and the implementation of the methods set forth herein after the application of "µ" and the calculation of a, b, L is obtained and tabulated with the equations above.

Figure 18:
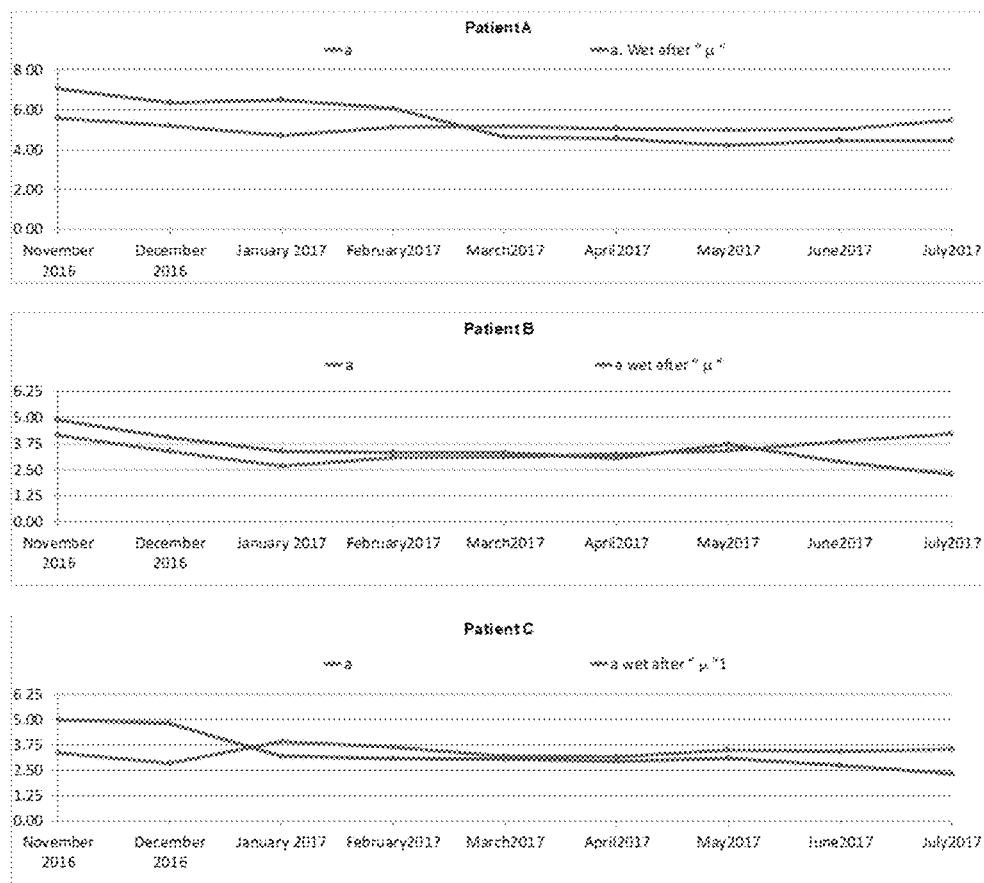
FIG. 18 depicts graphs reflecting data for three congestive heart failure patients.

With reference to the tables below and to FIG. 18, the three different patients (Patient A, Patient B, and Patient C) had new diagnosis of Congestive Heart Failure (CHF). Patient A, B, C have diastolic and systolic heart failure with an ejection fraction of 35% with normal coronary artery disease by angiography. All three patients were started on an angiotensin receptor blocker Valsartan and followed continuously every month for 9 months. The a, b, L were calculated before and after the "μ" has been applied shown in color red. The blue indicates the baseline. At the initiation of the CHF medication Valsartan, the patient has a normal response of the microvascular endothelium after the application of "μ" in the calculations of a, b, L. All colorimetric and spectrophotometric calculations are performed at the same location on the right arm, in the anterior position in all three patients continuously for 9 months. The titration of Valsartan was maximized in all three patients. The effects of the medication appear to demonstrate a decrease in the flow to the microvascular circulation of the endothelium at rest. This occurs because it is the desired effect of the CHF medication in the above patients over the period of 9 months. The current standard of care is to improve the heart function in CHF. The cardiologist lowers the ionotropic and chronotropic effect of the heart in CHF patients. The above methodology allows for the appropriate and desired effect in being able to titrate the medication and know how much medicine to administer to the patient by either decreasing or increasing the Valsartan dose. This is performed to achieve the necessary effect of pharmacotherapy with limiting the exacerbation of heart failure symptoms in such patients. It allows for healthcare providers to also know if the effects of the medications are adequate and they are in fact working appropriately on the microscopic endothelium level of the patient. As the months progressed in the patients above, the red line calculations indicate a decreased microvascular endothelial flow. This is evaluated by measuring a decrease in the a shift.

This correlates with a decrease in the ionotropic and chronotropic effect of the heart in these patients. This is the desired effect and outcome that the cardiologist is trying to achieve. The calculation of a, b, L, after "μ" is applied is objectively calculated in these CHF patients, allowing for the proper titration of maximum medication administration while limiting the side effects of the medications concurrently.

|  | November 2016 | December 2016 | January 2017 | February 2017 | March 2017 | April 2017 | May 2017 | June 2017 | July 2017 |
|---|---|---|---|---|---|---|---|---|---|
| Patient A | | | | | | | | | |
| Valsartan "δ" Administered for Congestive Heart Failure (CGH) | | | | | | | | | |
| L | 70.10 | 70.63 | 71.68 | 70.24 | 70.42 | 70.87 | 71.99 | 69.91 | 71.63 |
| a | 5.59 | 5.20 | 4.70 | 5.12 | 5.14 | 5.05 | 4.98 | 5.02 | 5.48 |
| a. Wet after "μ" | 7.06 | 6.35 | 6.48 | 6.08 | 4.64 | 4.54 | 4.20 | 4.43 | 4.46 |
| b Wet | 15.39 | 16.61 | 14.67 | 15.42 | 16.14 | 16.72 | 15.47 | 15.64 | 14.62 |
| L | 68.40 | 69.98 | 71.76 | 70.12 | 69.42 | 70.72 | 69.79 | 70.54 | 70.04 |
| a | 7.06 | 6.35 | 6.48 | 6.08 | 4.64 | 4.54 | 4.20 | 4.43 | 4.46 |
| b | 16.16 | 16.81 | 16.48 | 16.44 | 16.85 | 16.78 | 15.62 | 15.89 | 16.31 |
| Patient B | | | | | | | | | |
| Valsartan "δ" Administered for Congestive Heart Failure (CGH) | | | | | | | | | |
| L | 73.44 | 72.77 | 74.06 | 74.52 | 74.43 | 73.95 | 73.52 | 74.05 | 74.23 |
| a | 4.15 | 3.36 | 2.66 | 3.06 | 3.09 | 3.25 | 3.40 | 3.85 | 4.20 |
| a. Wet after "μ" | 4.89 | 4.04 | 3.37 | 3.3 | 3.29 | 3.03 | 3.71 | 2.88 | 2.25 |
| b Wet | 13.69 | 4.88 | 15.09 | 13.98 | 14.08 | 15.34 | 15.02 | 14.35 | 14.14 |
| L | 70.43 | 73.59 | 74.23 | 72.56 | 72.62 | 72.58 | 73.47 | 72.47 | 72.54 |
| a | 4.79 | 4.04 | 3.37 | 3.3 | 3.29 | 3.03 | 3.71 | 2.88 | 2.25 |
| b | 15.14 | 15.27 | 15.38 | 14.4 | 15.85 | 15.69 | 15.54 | 15.29 | 14.39 |
| Patient C | | | | | | | | | |
| Valsartan "δ" Administered for Congestive Heart Failure (CGH) | | | | | | | | | |
| L | 73.84 | 75.47 | 74.63 | 73.55 | 74.06 | 73.05 | 75.26 | 74.45 | 75.00 |
| a | 3.35 | 2.84 | 3.93 | 3.64 | 3.20 | 3.16 | 3.50 | 3.44 | 3.55 |
| a. Wet after "μ"1 | 4.99 | 4.84 | 3.18 | 3.07 | 3.05 | 2.95 | 3.1 | 2.75 | 2.3 |
| b Wet | 14.01 | 13.73 | 15.73 | 14.96 | 14.54 | 16.12 | 15.22 | 14.63 | 14.75 |
| L | 71.42 | 72.57 | 74.12 | 72.41 | 73.55 | 72.89 | 73.69 | 72.13 | 74.72 |
| a | 4.99 | 4.84 | 3.18 | 3.07 | 3.05 | 2.95 | 3.1 | 2.75 | 2.3 |
| b | 14.01 | 14.8 | 15.31 | 15.66 | 13.67 | 17.26 | 15.17 | 15.6 | 14.39 |

Titration of Medications:

Aspirin is a very common medication used ubiquitously throughout the world to treat a host of various diseases. The dose is always disputed and different publications, in different parts of the world, cite a different dose adjustment. The best dose that is administered is dependent on the patient and the effects of the anticoagulation strategy that is the desired outcome. In the past the system used was a blood assay that measured a calculation of the platelets aggregation units (pau). This value offers an assessment of the platelets clumping or stickiness that is achieved pre- and post-administration of aspirin. This then can be used to titrate the dose equivalent to the patient necessity based on the pau units. It is very cumbersome and extremely time-consuming process as well as invasive requiring multiple blood phlebotimizations in the patient In the micro-environment of the endothelium there is a constant cascade of clumping and disassociation of platelets occurring continuously. This again occurs on the cellular platelet level thus allowing for the micro clotting and lysis to occur continuously. Aspirin will benefit patients by decreasing the effects of these actions from occurring. Therefore, aspirin will allow for a decreased amount of platelet clumping and better flow through the microvascular circulation. The dose is not known exactly for each patient's benefit and because of the risks that are also associated with aspirin usage (i.e., gastritis or stomach ulcers), the standard dose is 81 mg in the United States or 100 mg in Europe. The above methodology that is described herein can be applied and calculated to ascertain which dose would benefit the patient depending on which dose can improve the flow of the microcircuits in the endothelial environment. This will therefore demonstrate the possibility of calculating which dose of aspirin will increase the flow to that area and therefore increase the percentage change equal to or greater than 10%. This will then allow the patient or the healthcare provider, by titration, to get the appropriate dosage that is most beneficial to that patient while maximizing the benefit and minimizing the risks that are associated with various medications. The titration will be different for each patient that could be evaluated and tracked closely non-invasively because the absorption of the medication will also be changed dependent on the status of the gastrointestinal system at that time that can always decrease or increase the absorption effects of the medication affecting the bioavailability of the quantity of medication in the blood stream at any given time.

If the effect of the administered drug has not changed the flow color to equal to or greater than 10% after drug "$\mu$" is administered after 5 half-lives drug "$\delta$" then the patient or the physician may have a benefit of increasing the dose or deciding to change the medication to a more suitable class of medications that would benefit the patient and his overall risk profile.

The method described above can objectively quantify the overall effects of the medication and be used to adequately treat disease processes even when there is no subjective difference the patient ascertains while on the medication Peripheral Artery Disease When the arteries in the lower extremities become blocked and stenosed with various disease manifestations such as diabetes, hypercholesterolemia there is an increased amount of claudication that occurs with the lower extremities with minimal exertion. Using the current methodology described herein the patient can ascertain if the effects of the various antiplatelet and statin medication's i.e. Lipitor, Crestor are affective in improving the blood flow to the lower extremities. By taking baseline measurements in the lower extremities in particular locations in the legs such as the anterior tibial surface of a right or left leg, medication can be then administered to the patient. After the corresponding 5 half-lives or more have past of drug "$\delta$" the procedure above can be implemented and test run to determine the a, b, L after drug "$\mu$" has been applied. This information can then be used by calculating the measurements with the equation as described above the change in the colorimetric and spectrophotometric variables that can be derived. This will then allow for the ability of the patient in the healthcare provider to know which drug provides the maximum increase in cardio vascular flow to the area based on the information of the homeostasis of the microvascular endothelial system. The more a percentage change of equal to or greater than 10%, the better the flow that would be understood to be an improvement of the peripheral circulation of that area. It will also allow for the proper titration of medication of that particular area. If it seems to improve the flow then, the patient and the healthcare provider may decide to increase the dosage of the medication to have a better benefit. This will allow for an objective determination of how well the patient is responding to the medication while minimizing the side effects of the drugs.

If the blood circulation flow was worse there would be no change or a negative percentage decrement that would be calculated. This would therefore allow the patient to know to alter therapy because the medication may not be effective or work for that patient. This procedure would also allow for the interventional angiologist to know which arterial distribution has the worst flow parameters. This methodology can be correlated with the angiogram of the peripheral circulation to know which artery would need to be angioplastied (stent placement in the stenosed artery) to have the best improvement for the patient symptom of claudication. The Where is the Flow that is calculated the worse the ischemic burden and stenosed artery to that particular peripheral muscle group in the Peripheral extremities. Therefore, the interventionist will have more objective evidence of which Artery needs to be intervened upon (the artery that would benefit from a balloon and or a stent).

Figure 19:
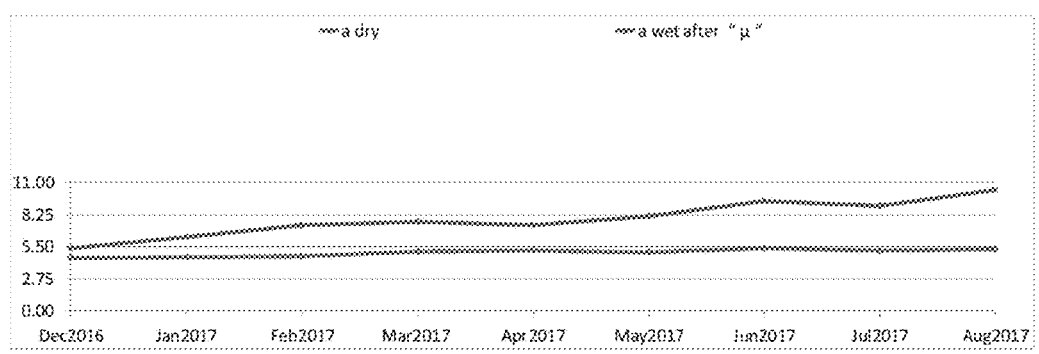
FIG. 19 depicts a graph reflecting data for a peripheral artery disease patient.

With reference to the table below and to FIG. 19, the table and the graph show a patient with known peripheral artery disease diagnosed by angiogram in the right distal common femoral artery who is having his right anterior thigh continuously evaluated at the same location for the a, b, L calculations after he was initially started on 50 mg of cilostazol twice a day from December 2016 until August 2017. The values of the of a, b, L, are calculated after "$\mu$" was applied which is shown in color red. The blue represents the baseline of the calculation of a, b, L. The greater the value of the a shift after application of "$\mu$" demonstrates the increased and improved blood flow to the microvascular endothelium. This demonstrates a greater red color indicating improved blood flow after the administration of the medication and continuous monitoring for 9 months after the initiation of the cilostazol treatment.

|  | December 2016 | January 2017 | February 2017 | March 2017 | April 2017 | May 2017 | June 2017 | July 2017 | August 2017 |
|---|---|---|---|---|---|---|---|---|---|
| Cilostazol "δ" | | | | | | | | | |
| L | 65.09 | 58.14 | 71.68 | 70.24 | 70.42 | 69.91 | 66.06 | 71.63 | 65.59 |
| a dry | 4.58 | 4.62 | 4.70 | 5.12 | 5.14 | 5.02 | 5.35 | 5.15 | 5.31 |
| a wet after "μ" | 5.35 | 6.33 | 7.33 | 7.62 | 7.33 | 8.06 | 9.40 | 8.95 | 10.32 |
| b | 15.65 | 10.51 | 14.67 | 15.42 | 16.14 | 15.64 | 17.75 | 14.62 | 16.8 |

Monitoring of the Homeostasis of Patients in the CCU, ICU, Emergency Room or Operating Room By having this monitor and performing the above methodology, on a patient with continuously recording and calculating the measurements, the patient who is located in the above-mentioned areas of the hospital can be continuously monitored. If there is any change of baseline hemodynamics status, it can be immediately detected because there will be a decrease in the percentage calculation after drug "μ" is applied. If the patient cardiovascular system has a collapse that it cannot sustain the blood pressure, the cardiovascular system will immediately have a change in the myocardial wall motion augmentation that will immediately cause a decrease in the cardio vascular flow to the microcirculation of the endothelium. This will therefore decrease the calculations described above to less than a 10% or more decrease which will then be able to signify to the patient and the healthcare provider that a change in cardiovascular status is occurring. This will be able to occur in a very rapid response because the augmentation of the myocardium will immediately reflect the decreased flow to the endothelium and immediately decrease the percentage of micro vascular flow. This will allow the patient and the healthcare provider to immediately respond to the patient's needs. Because Tachycardia and respiratory rate can be dramatically affected by the patient's anxiety level or pain level they do not necessarily correlate with the change in the myocardial augmentation and hence the flow to the micro vascular circulation of the endothelium. Therefore, anxiety levels nor pain thresholds will not cause a collapse in the cardiovascular system in contrast to sepsis, myocardial infarction, stroke, hematoma or internal bleeding, etc. which will cause a collapse of the hemodynamic system. By applying the means and methods described above it will be possible to determine the cardiovascular status and homeostasis of the patient separate from the heart rate and the respiratory rate which may be directly impacted by the anxiety or pain level of the patient when the patient is located in the monitored hospital or office setting such as CCU, ICU, operating room, ER, or the like.

This form of measurement in calculation described above will not be affected by other etiologies such as anxiety. Therefore, it will allow a continuous means of assessment of the patient's baseline homeostasis. The same means and procedure will be applied as described above herein, in a continuous flow of information that will be examined and calculated with the colorimetric and spectrophotometric method.

Evaluation of Bronchodilators and Inhalers

After the administration and treatment of asthma and Chronic obstructive pulmonary disease with inhalers and bronchodilators, the treatment of these medications to these diseases above can be further assessed. After the treatment with the inhaler and or nebulizer with the above-mentioned process, the evaluation of the a, b, L before and after the treatment with the inhalers and or nebulizers, as well as the application of the p drug and then measurement method of the a, b, L measurement will allow for further evaluation of the effectiveness of the inhalers and or nebulizers by the patient. The effects of these medications again should improve the micro vascular blood flow to the endothelium changing the color and hence changing the effect of the a, b, L, after the methodology described above with "μ" is applied. This will allow the patient and the health care provider to adjust the type of inhaler and or nebulizer and the dose that is needed to effectively treat the patient appropriately. The measurements and the calculation described above will allow the patient to have a determination of the appropriate dose and type of inhaler and or nebulizer. The micro endothelial environment will be directly and proportionately affected. The constriction and dilation of the endothelium will be directly influenced by the oxygenation of the cells. Hence the constriction or dilation will be easily evaluated and measured with the above method measuring and calculating the a, b, L after the application of the "μ." Then, the flow in the endothelial micro capillary system will be further clarified allowing to determine the appropriate treatment strategy and dosage of inhalers, nebulizers and bronchodilators for patients that are suffering from respiratory diseases.

Evaluation of Chemotherapy Medications

Every day patients are exposed to therapeutic treatment modalities with chemotherapeutic medications such as antibiotics for infections or chemotherapeutic modalities e.g. including but not limited to Adriamycin, bleomycin, Herceptin® (trastuzumab) for oncological or hematological diseases or medications such as anti-tumor necrosis factor blockers e.g. Humira® (adalimumab) or Enbrel® (etanercept) for inflammatory diseases such as arthritis, psoriasis, eczema or chrons disease, ulcerative colitis. All medications (δ) that are given by oral, dermal or infusion will affect the cardiovascular system. The drugs which are including but not limited to the ones above will have a deleterious effect on the cardiovascular system of the patient. The current modality of evaluation is to follow up the patient based solely on symptomotology which will be totally subjective and prone to many biases. The other method is to measure the total body surface area of the patient and limit the exposure to the drug based on the maximum allowable administration of the desired δ in mg per kilogram dependent on the Body surface area. For example, the cumulative doses of Adriamycin above 550 mg/m2 are associated with an increased risk of cardiomyopathy and deleterious consequences of the vascular system in the patient. This will be ascertained based on the Body surface area of the patient. This is the only method that is currently used to determine the amount of drug that can be administered as well as symptomotology that the patient expresses to the healthcare provider. This methodology is flawed because it assumes that all patients are exactly the same and all patient will respond exactly the same to the therapeutic effects of the administered drug δ. Healthcare professionals know that individual patients respond differently and some patients may suffer a more deleterious effect of δ from a smaller dose of 550 mg/m2 and some patients may have no deleterious effect from a higher administered dose of 550 mg/m2 which will therefore limit the amount of proper therapeutic administration of δ that can be given to offer a better chance to such patients to combat the different diseases, such as cancers.

By implementing the above-mentioned practices and methodology, the healthcare professional and the patient can directly use the method described above to constantly derive the status and the function of the endothelium and hence the cardiovascular systems health of every single patient. These are molecular drugs, δ, that are given as therapeutic modalities. They will affect the microvascular health of the patient first and the health of the endothelium first on a microscopic level. Therefore, the flow of the endothelium will be altered based on the increased resistance that will take place because of the deleterious consequences of drug δ impact on the endothelium. Therefore, since the flow will change the color will change. This is the first thing that will have an objective response to administered δ that can be followed and tracked individually based on every single patient with their healthcare provider. Once the microvascular flow changes on a microscopic level this will be evaluated by a color shift that will inform the patient of a greater problem that can be looming before subjective symptoms arise or end stage clinical manifestations occur such as cardiomyopathy or allow the treating physician to increase the dose of the δ to further attack the disease such as the cancer because no deleterious effects have yet occurred. It allows for a more fine and detailed response that can continuously monitor the endothelial health of the patients and tailor a more precise treatment strategy and protocol to each individual patient. This methodology for the assessment of clinical δ drug effectiveness and resultant impact on the cardiovascular system is unique in medicine for its high degree of specificity and sensitivity.

The same principals apply to mucous membranes as to skin, with the added advantage that the underlying vasculature (e.g. capillaries) are more exposed to the surface than in typical skin (e.g. on the upper back). This provides more pronounced color changes and differentiation than is obtained from regular skin. Further, for wet runs, mucous membranes can have greater drug permeability. The disadvantage of mucous membranes is that their locations often makes color detector positioning and monitoring more difficult and less practical. Nevertheless, the substitution of mucous membranes in place of patient skin is within the scope of the invention, and should be considered disclosed for all embodiments where practicable.

Typically, and preferably, when a series of skin redness measurements are being made and compared, the same area of skin should be observed each time. Different areas of skin on a given individual can have different shades and other variables (hair, texture etc.). Observing the same location minimizes the chance that factors other than perfusion, dilation, blood oxygenation etc. will result in different color readings between measurements. For example, if a patient is undergoing stress tests before and after being administered a pharmaceutical, the color detector(s) should be in the same location for each test. This ensures an "apples to apples" comparison.

Figure 6:
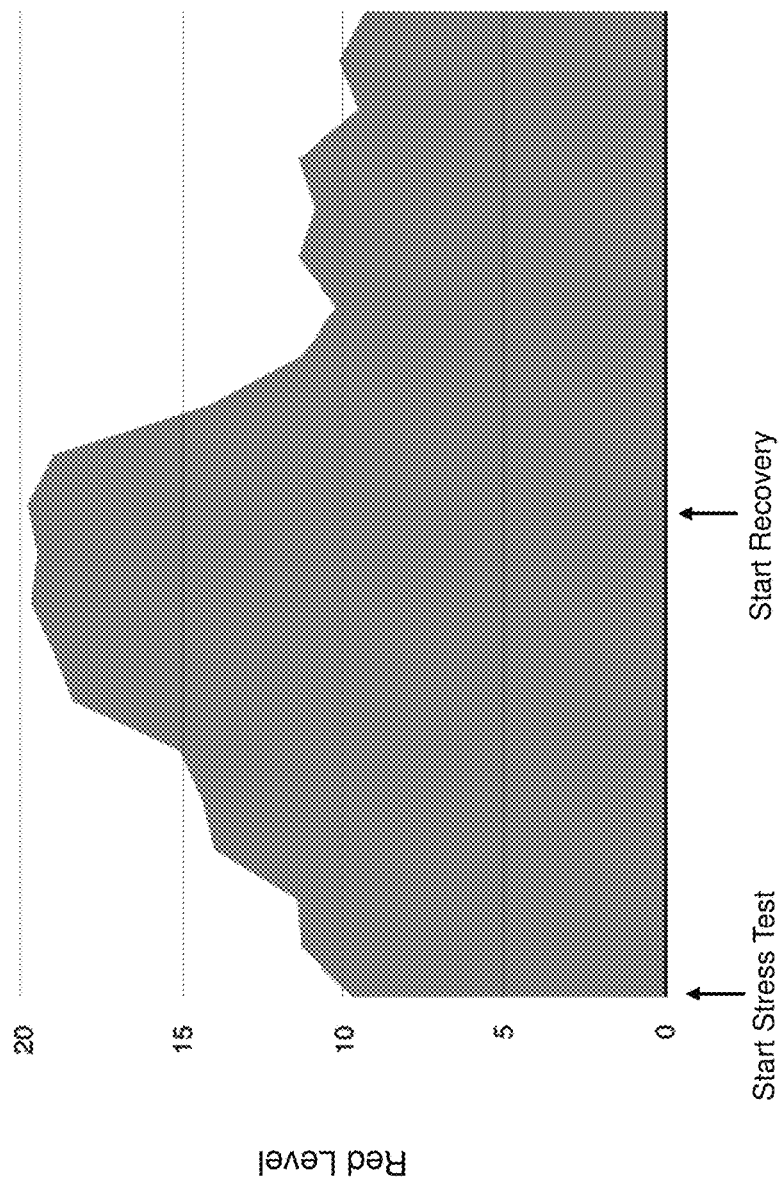
FIG. 6 is a graph of red shift data for a very healthy patient during a stress test.

FIG. 6 is a wet run stress test curve showing red shift for a 40-year-old Marine who is in excellent cardiovascular health. The curve shows a substantial and rapid increase in redness (redness A roughly doubling), followed by a rapid return to pre-exercise skin color and perfusion when exercise ends.

Figure 7:
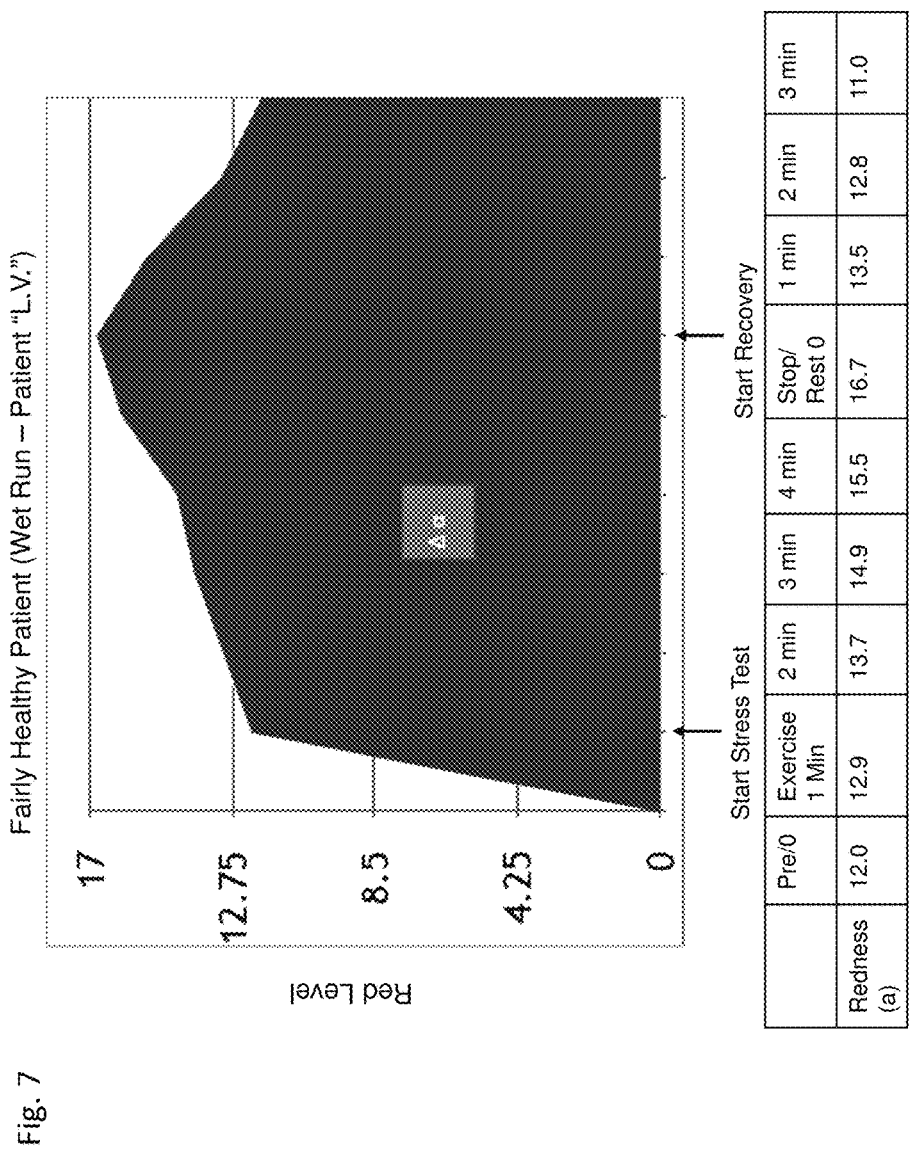
FIG. 7 is a graph and table of red shift data for a moderately healthy patient during a stress test.

FIG. 7 is a wet run stress test curve for a patient L. V. who is in reasonably good cardiovascular health, though to a lesser extent than the Marine in FIG. 6. Skin redness increases by approximately 39% from exercise start to peak.

Note: The first portions of the graphs in FIGS. 7-10 showing increases starting from zero redness are artifacts and do not reflect patient data (skin redness will rarely, if ever, be zero).

Figure 8:
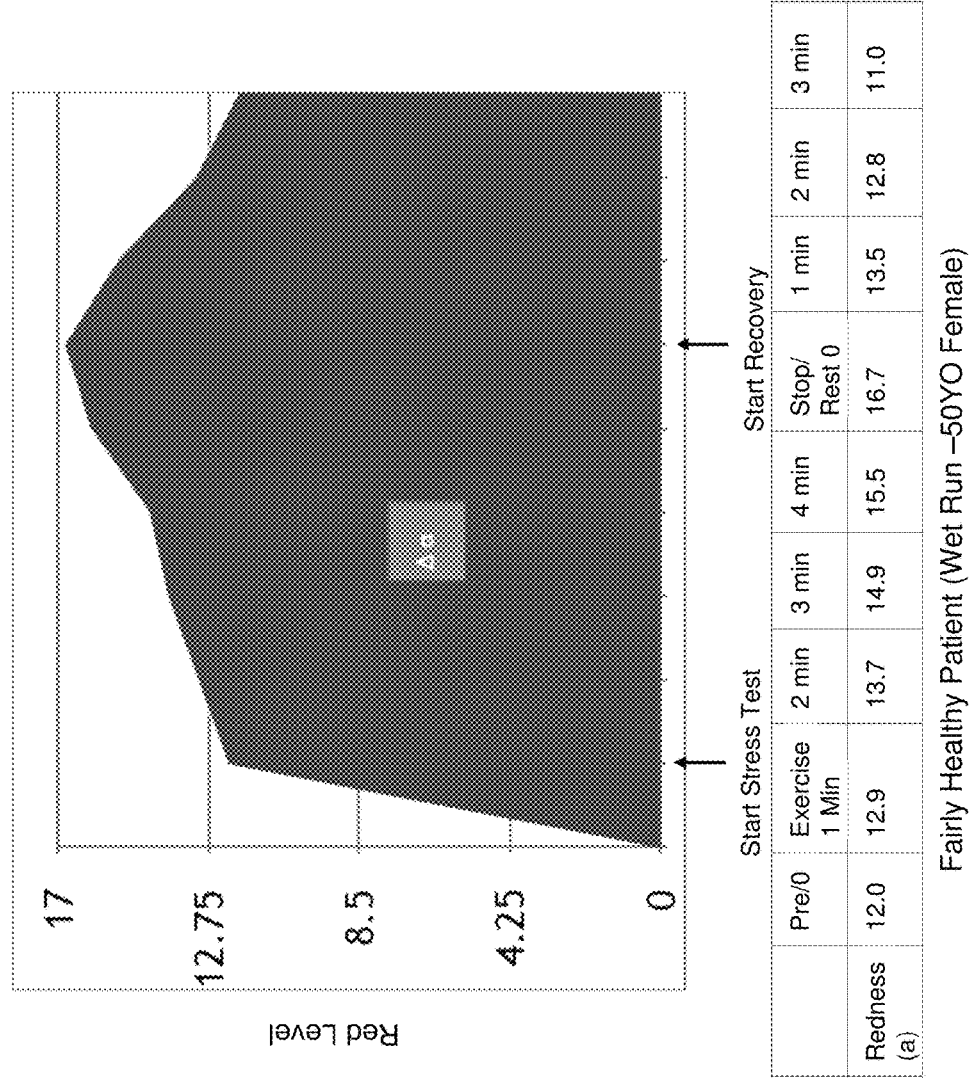
FIG. 8 is a graph and table of red shift data for a second moderately healthy patient during a stress test.

FIG. 8 is a wet run stress test for a 50-year-old female also in a reasonable state of health. Skin redness increases approximately 66% from baseline to maximum.

Figure 9:
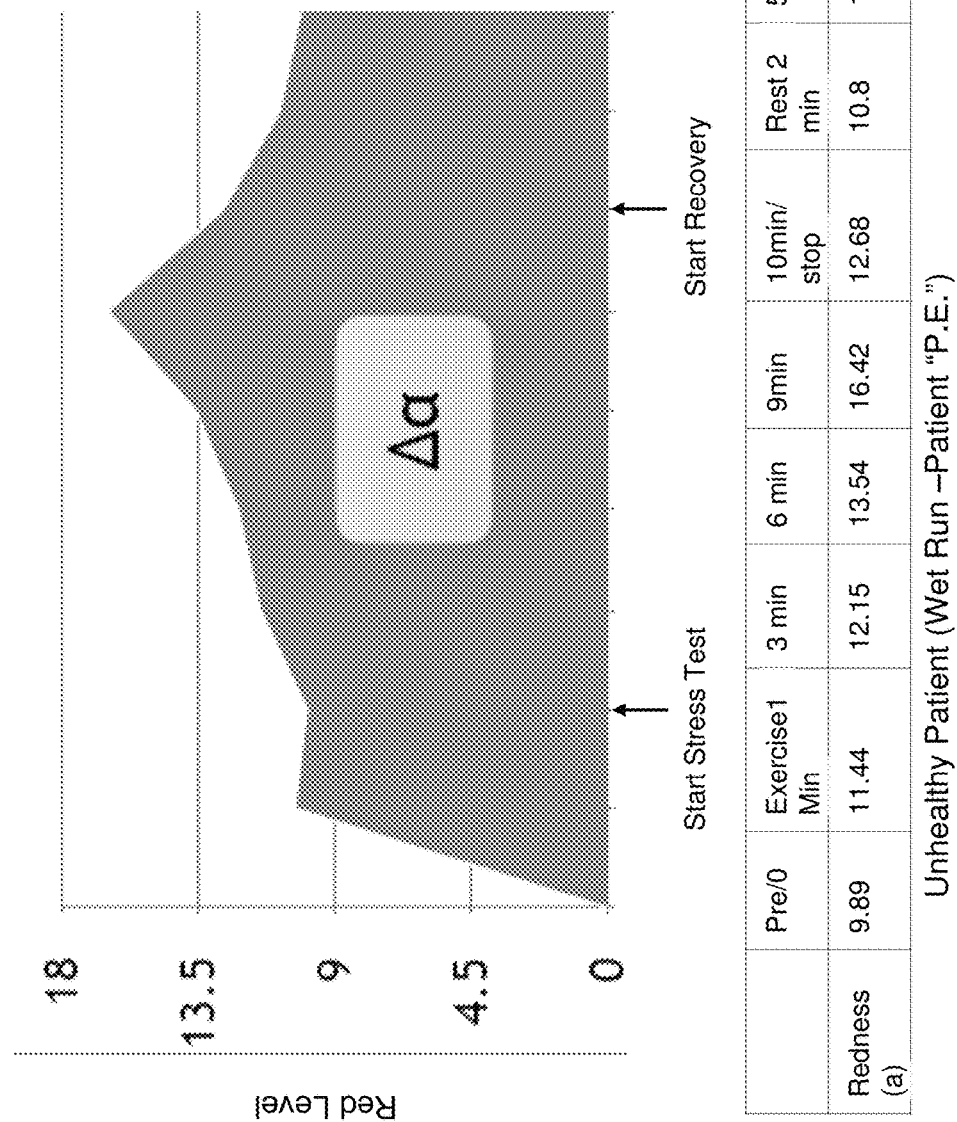
FIG. 9 is a graph and table of red shift data for an unhealthy patient during a stress test.

FIG. 9 is a stress test for unhealthy patient P. E. Skin redness actually declines by approximately 24% over the course of the stress test.

Figure 10:
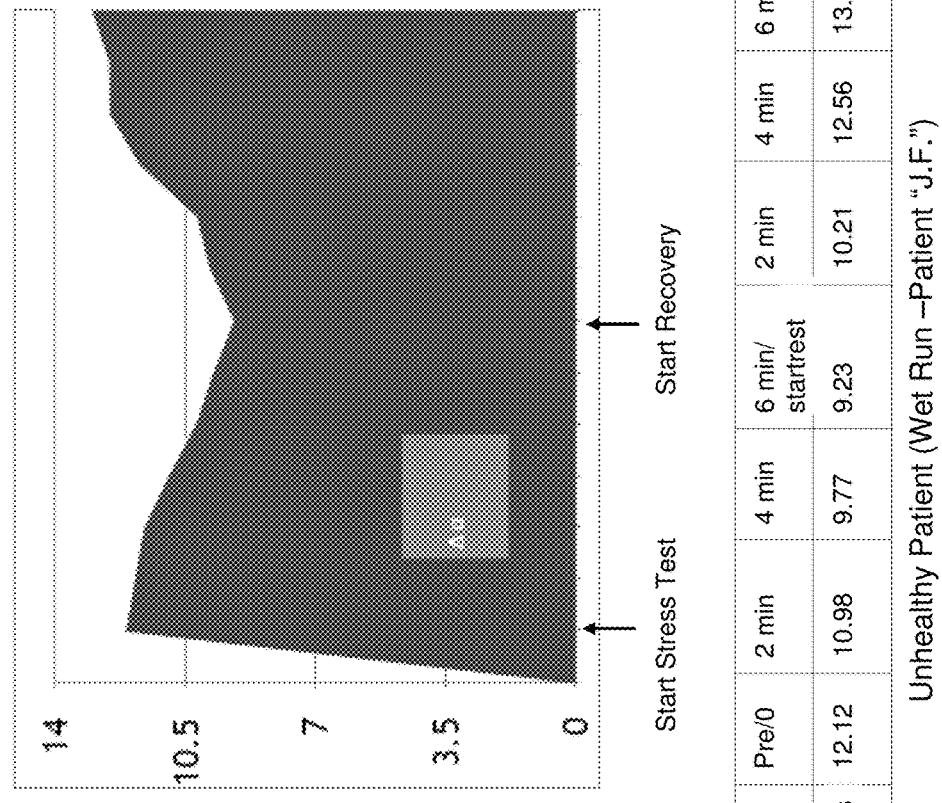
FIG. 10 is a graph and table of red shift data for a second unhealthy patient during a stress test.

FIG. 10 is a second unhealthy patient J. F. Skin redness declines by approximately 57%.

The principles and methods of this invention have been developed working with a large number of patients, and the specific patients and data shown FIGS. 6-10 are selected as illustrative examples.

Cardiovascular health as estimated by stress test red shift has been found to correlate well with cardiovascular health as determined with other more traditional methods, and has good predictive value when follow-up diagnostics are performed.

Dry Run Method

A "dry run" procedure refers to monitoring and diagnosis steps according to the invention which are performed without applying a chemical solution to the area of skin being observed by the color detector. Dry runs are sometimes used (as opposed to wet runs) for simplicity, such as when applying a chemical solution would be inconvenient or impractical. For example, it may be more practical to use dry run conditions when performing long term monitoring outside of a medical environment using a portable color detector.

An exemplary dry run is performed in a stress test lab in a medical facility. Before the procedure vital signs may be checked: e.g. heart rate, oxygenation, and EKG (baseline). Next, a baseline resting color detector reading is taken. For example, L/a/b values can be recorded at baseline at the patient's upper scapula, preferably while they are sitting or standing still and their heart exertion is at resting levels.

The patient then begins a stress test exercise regimen, such as the "Bruce protocol" which uses a treadmill. The Bruce Protocol is a three-minute interval stress test, starting at 10% incline at 1.7 miles per hour, changing to 12% incline after three minutes, increasing to 2.5 miles per hour changing to stage three, then 14% incline at 3.4 miles per hour, then 16% incline at 4.2 miles per hour, and then 18% incline at 5.1 miles per hour. Speed and incline can increase indefinitely in theory, though in practice patients actually needing stress tests generally cannot go beyond 18% incline and 5.1 miles per hour. The Bruce Protocol is only a preferred example, and other stress test protocols can be used with the invention. For example, exercise time intervals in the ranges of 10 seconds-10 minutes, 30 seconds-5 minutes, 1 minute-4 minutes, or 2 minutes-4 minutes, raising exercise resistance and/or speed at each interval. The exercise protocol can include the patient using, for example, a treadmill, a stationary bicycle, an elliptical trainer, an arm ergometer, or other known exercise devices.

Color detector readings are made at regular intervals during the stress test. For example, L/a/b readings (or just a readings or red light readings) may be taken every minute of the Bruce protocol starting at time 0. Other vitals (blood pressure, heart rate, EKG, etc) can also be measured throughout the procedure at the same or different intervals, along with subjective statements regarding how the patient feels such as chest discomfort or shortness of breath. Reading interval ranges of every 30 seconds to every 2 minutes, every 30 seconds to every 4 minutes, and every 10 seconds to every 5 minutes are examples within the scope of the invention.

The exercise portion of the test typically ends when the patient indicates they want or need to stop, but can also be ended at "peak exertion". The patient immediately sits down, which begins the recovery portion of the procedure—i.e. recovery time 0. A color detector reading is made, as well as any vitals as described above and a subjective evaluation of how the patient feels. Periodic readings continue during the recovery period. For example, every minute up to 10 minutes in recovery.

Color detector readings are preferably taken at the identical site on the patient throughout the exercise and recovery portions of the procedure. For example, on the right superior portion of the scapula, or on the arm or wrist using a worn color detector.

In some embodiments, myocardial performance index (LV) (Tei Index) is evaluated before and after each run. Tei Index is an index that incorporates both systolic and diastolic time intervals in expressing global systolic and diastolic ventricular function. Determining Tei Index describes the systolic (squeezing) and diastolic (relaxation) function of the heart and is correlated with the values of the color detector.

Wet Run Method

"Wet runs" can be performed according to the same general protocol described above for dry runs, which are incorporated herein but will not be fully repeated for brevity. The difference is that for wet runs the skin area being measured with the color detector is wetted with a chemical solution (a.k.a. "Wet run solution"). For example, a solution of one or more chemicals (e.g. acetylcholine and/or thrombin) in water, alcohol, petroleum jelly, or saline. The solution can be applied by wiping or covering the area with a wet gauze pad. The solution may be applied once at the beginning of the procedure before the color detector is positioned on the skin, or applied more than once throughout the procedure. Suspensions of effective chemicals (as opposed to solutions), viscous spreadable chemical applications, lipid-carrier compounds, and potentially non-wet applications of effective chemicals are also contemplated.

As mentioned, skin redness increases both more, and more quickly, in healthy patients than in patients with vascular disease. Acetylcholine (and other applicable chemicals) increase the color contrast between healthy and unhealthy individuals, which has been found to facilitate better colorimetric diagnoses. For example, in a healthy individual, the positive red shift (a.k.a. "alpha shift", a.k.a. $\Delta$a) is greater at a given exertion level in a wet run than in a dry run. An unhealthy individual, in contrast, will still have low, negligible, or even negative red shift during exercise in a wet run. Wet run methods, when available, are generally preferred to dry runs because they increase the color difference between healthy and unhealthy individuals.

Wet runs can also be used as a partial substitute for exercise in a clinical setting, such as for patients who are not physically able to perform stress test exercises. The chemical alone provokes the same general types of differential responses as stress test exercise. For example, in a healthy at-rest individual, acetylcholine alone causes skin capillary dilation, which increases blood perfusion and (because blood is red) causes the skin to become more red. In an unhealthy individual, the acetylcholine alone will cause only low, negligible, or even negative red shift. Thus, the differential reactions to application of acetylcholine (for example) can be used to assess vascular health or the effectiveness of medication even without a stress test.

Acetylcholine is understood to dilate normal blood vessels, but to not dilate or to constrict vessels subject to various deleterious conditions such as stenosis. See discussion of *Paradoxical Vasoconstriction Induced by Acetylcholine in Atherosclerotic Coronary Arteries* above. Without intending to be bound by theory or to limit the scope of the invention, the instant methods and solutions take advantage of related properties understood to exist in skin capillary vasculature.

In both wet and dry runs, each procedure can be repeated more than once in order to confirm results, reduce testing error, and identify less reliable outlier data.

Wet run solution is typically applied to a relatively small area of the patient comparable to or somewhat larger in size than the input window of the color detector to be used for the wet run. For example, wet run solution may be applied to a body area of 1-10, 1-100, 0.1-100, or 1-250, or 5-400 square centimeters.

Wet run solution is preferably applied to the skin shortly before wet run monitoring begins. For example, the same day as the wet run, less than an hour, less than twenty minutes, less than five minutes, or less than one minute before the color detector is positioned over the area and/or the wet run color detector monitoring begins. Additional preferred time ranges for applying wet run solution are 1-60 seconds, 1 second-five minutes, 1 second-20 minutes, 10 seconds-10 minutes, 30 seconds-20 minutes, 1-10 minutes, and 1-60 minutes before monitoring.

Chemical Stress Testing

Pharmaceutical stimulation can be used instead of exercise for patients who would have difficulty using a treadmill or other exercise methods. Chemical stress tests typically use intravenous medication (e.g. dobutamine, dipyridamole, or adenosine) with an imaging technique (isotope imaging or echocardiography). The medication increases the heart load, as opposed to physical exercise. The chemical stress causes normal coronary arteries to dilate, while the blood flow in a blocked coronary artery is generally reduced. This reduced blood flow in the blocked artery reduces movement of the affected wall (as seen by echocardiogram), or reduces isotope uptake (in a nuclear scan).

Dry and (preferably) wet run color detector observation can both be used to measure red shift before, during, and after chemical stimulation in chemical stress tests, applying the same principles and general methods. Patients in better cardiovascular health are expected to have greater positive red shift in response to chemical stimulation than patients in poor health. Color detector measurements can be made before chemical stimulation (baseline), at intervals during chemical stimulation, and after chemical stimulation is ended. Color detector monitoring can be applied in addition to traditional EKG and/or imaging monitoring, or on its own.

The invention includes use of chemical stress testing together with wet run methods, and with simultaneous wet run/dry run comparison methods discussed in greater detail below. Stress testing with red level monitoring can be used before and after administering a pharmaceutical to determine efficacy.

Wet Run Solutions

As mentioned above, acetylcholine solutions can be applied to the skin to increase the color contrast between healthy and unhealthy individuals, which has been found to facilitate better colorimetric diagnoses. Colorimetric monitoring procedures which include the use of such chemical solutions are described generally as "wet runs". Chemical solutions for use in wet runs may also be termed "wet run solutions".

Wet run solutions can be applied to the area of skin being monitored in a variety of forms and regimens. Typically, the wet run solution will be applied to the skin, and then the color detector is positioned on the skin either immediately or after a short waiting period for the solution to soak in and take effect. In longer procedures the solution may be applied repeatedly as needed.

Wet run solution may be applied by various known methods. A gauze pad or other absorbent material is wetted with the wet run solution, and then wiped over or held against the skin. For example, an item soaked in wet run solution may be held against the skin for at least 5, 10, 30, or 60 seconds. The solution may also be brushed or sprayed on.

In one illustrative example, a half cup of 70% isopropyl alcohol is mixed with a half teaspoon of acetylcholine to make a wet run solution. Wet run solution may be prepared daily or even for each patient depending on circumstances. Wet run solutions with the following chemical amounts (by weight compared to total carrier/solvent) are contemplated as non-limiting examples: 3-5%, 1-5%, 1-10%, 0.1-10%, 0.1-25%, 0.01-5%, 0.01-25%, 5-50%, at least 0.1%, at least 1%, at least 5%, at least 10%, and at least 20%.

While acetylcholine is a preferred wet run chemical, other drugs which affect endothelium constriction ("endothelial stimulatory compounds") can also be used. The important factor is that the chemical(s) cause endothelium in both the arteries and capillaries to dilate in healthy individuals, but not (or to a lesser degree) in individuals having vascular disease. Endothelium-dependent vasodilators are generally understood to be useful wet run chemicals. Endothelium-derived relaxing factors (EDRF) are produced and released by the endothelium to promote smooth muscle relaxation. The best-characterized EDRF is nitric oxide (NO). Without limitation, the following are also believed to be useful as wet run chemicals individually or in combinations: adenosine, Vasopressin, nitroglycerine, persantine, acetylcholine, serotonin, bradykinin, nitric oxide derivatives (e.g. Viagra® (sildenafil), Cialis® (tadalafil), Levitra®, (vardenafil)), phosphodiesterase type 5 (PDES) inhibitors, mergonavine, ergometrine (a.k.a. ergonovine), arginine derivatives, citruline derivatives, thrombin, thromboplastin, L arginine and arginine derivatives, thiols, cysteine, glutathione, peroxynitrite, cysteine, glutathione, peroxynitrite, nitrosates, nitrosites, nitrosates glucose, nitrosates glucose, nitrosyl glucose, and/or transnitrosates. Wet run solutions including these chemicals, and wet run procedures using such wet run solutions, are contemplated for implementing the invention.

We recommend that when there is doubt, candidate chemicals can be evaluated as wet run chemicals by testing them on the skin of individuals known to have and not have vascular disease, and to confirm the presence of differential dilation (as measured by red shift) between those individuals as disclosed herein. Further, candidate chemicals can be evaluated by testing differential dilation effects when the chemicals are injected into coronary arterial circulation. See *Paradoxical Vasoconstriction Induced by Acetylcholine in Atherosclerotic Coronary Arteries* cited above. Candidate chemicals may be confirmed as having differential dilation in healthy vs. vascular disease patients in both the capillaries and the coronary arteries. This has the added advantage of confirming parallel reactions in the coronary arteries and the skin capillaries.

Various solvents or carriers can also be used. For example, water, alcohol (e.g. isopropyl, ethyl, methyl) alone or mixed with water, saline, phenols or phenol-derived solvents, petroleum jelly, lipids, and oils. Suspensions and dry and wet mixtures are also contemplated as alternatives to "wet run solutions", so long as safe and effective delivery of one or more wet run chemicals to the skin is accomplished.

The wet run solution may advantageously be viscous, as opposed to fully liquid, for some applications. Viscous solutions can be prepared using a viscous solvent or carrier (e.g. petroleum jelly, oils, or other lipids), and/or high concentrations of chemical and relatively lower amounts of solvent. Viscous wet run solutions can stay on the skin for longer periods without running off or evaporating. Viscous wet run solutions may be used to provide a supply of chemical to the skin over longer periods than conventional liquid solutions, providing some "extended release" function. For example, a viscous wet run solution (e.g. acetylcholine in petroleum jelly) may be applied as a thin layer on the skin and a color detector then placed over the same area to perform an extended wet run. For example, wet run solutions having total viscosities of at least 0.1, 0.5, 1.0, or 2.0 Pa·s at room temperature are contemplated.

Wet run solutions (or mixtures, emulsions, etc.) using hydrophilic carriers or solvents are also contemplated. Hydrophilic carriers are useful to increase the skin and cell permeability of the wet run solutions for improved transdermal drug delivery. For example, oils, fats, petroleum jelly, or paraffin. Some hydrophobic carriers/solvents will provide similar staying power/extended release advantages as viscous carriers/solvents discussed above.

In clinical trials wet run solutions have been prepared daily and/or for each new patient, although such is not a requirement.

Wet run solution may be provided via a disposable transdermal patch, which may be positioned on the skin using adhesive.

Wet run solutions and chemicals can also be applied to a garment, arm band, sorbent patch or other carrier which can be worn against the skin. The wearable item may be combined with a wearable color monitoring device so that wet run chemicals are provided to the skin in the immediate vicinity of the monitoring device, or could be worn and then removed before wet run color readings are taken. Wet run chemicals may be provided to the wearable carrier as a solution, slurry, or other wet preparation. Alternatively, undissolved or dry "wet run" chemical can be provided in the carrier or patch to be dissolved as the patient sweats during exercise, facilitating skin absorption.

Aspects of this invention thus include wearable items which incorporate both wet run chemicals and one or more color detectors positioned adjacent the same area(s) of the wearer's skin (e.g. adjacent, or within 1 or 0.5 inches), and methods using such wearable items. One embodiment is a garment including a wet run color detector adjacent a wet run carrier holding wet run chemical, and a dry run color detector at a different location. In a preferred embodiment the color detectors are positioned in the garment (e.g. a shirt) near a user's back, upper back, or shoulder blades in mirror-image locations. The garment can be shaped and sized to hold the color detectors and carrier against the skin, and/or adhesives could be used to maintain the items against the skin.

Example 1—Stress Test Protocol

A 30-year-old patient is administered exercise stress test and EKG. The patient exercises for a total of 15 minutes pursuant to the Bruce Protocol. Color detector readings are taken on hairless area of rear shoulder or other accessible and hairless area. Baseline color detector L/a/b reading of skin color is acquired before Bruce Protocol stress test is initiated. The patient is started on treadmill at 1.7 mph, which is increased over time per the protocol. L/a/b color detector readings are taken at one to three-minute intervals during the duration of the protocol, and when patient ends the exercise. When exercise ends, patient sits down to begin the recovery phase. Color detector readings continue every one to three minutes for a five to twenty minute recovery phase.

EKG is also monitored during exercise and recovery phase, and ST-T wave irregularities, if any, are identified. Doppler ultrasound imaging is also used during recovery and correlated with EKG to identify abnormalities. Specifically, tissue Doppler indices are evaluated on the septal and lateral wall of the left ventricle underneath the mitral valve. This allows the replication of objective evidence of ischemic thresholds seen on standard cardiovascular testing to be compared to the color detector data.

A dry run can be employed in the exercise and recovery phases, where the color detector is placed directly on patient skin during stress test and recovers.

A wet run is employed instead of or in addition to the dry run. In wet run a gauze pad soaked with chemical solution (e.g. acetylcholine in alcohol) is placed on the area of skin to be monitored. For example, application may be for 30 seconds, for 10 seconds to three minutes, for at least 5 seconds, for at least 15 seconds, or for another period of time. Once the pad is removed the color detector is applied and color readings are made as described above.

Both wet and dry runs may be simultaneously used during the stress test and recovery. For example, using two color detectors, one on each shoulder blade, during exercise and recovery.

Example 2—Color Detector Stress Test Identifies Coronary Artery Disease

A patient underwent a treadmill stress test with both wet run colorimetric and (standard) EKG and image (echocardiograph) monitoring. Standard EKG and image results indicated normalcy. However, colorimetric spectrophotometer showed a negative red shift in the skin during a stress test, which (correctly) indicated severe deficits in perfusion of the coronary circulation and arterial circulation of the heart. Follow-on examination determined that the patient had balanced ischemic heart disease (i.e. disease causing decreased blood flow to all three coronary arterial areas of the heart). Thus, in this case the colorimetric stress test correctly identified severe coronary artery disease which was missed by standard stress test methods.

Administering and Testing Medication

The effects, effectiveness, and correct dosing of medication can vary substantially between individuals, and colorimetric analysis according to this invention is useful to measure and quantify individual reactions based on endothelial response and skin capillary dilation. Positive effects can be identified and confirmed, e.g. by increased red shift during exercise. Colorimetric methods can be used to identify a minimum dose needed to achieve a peak or satisfactory improvement, as determined by improved red shift. This allows the physician to maximize positive results, while avoiding side effects and/or toxicity from unnecessarily high drug doses.

Color detector methods according to this invention are particularly relevant to medications which treat vascular conditions such as statins, including Atorvastatin (Lipitor®), Rosuvastatin (Crestor®), simvastatin, and pravastatin and the like to therapeutic treatment modalities with chemotherapeutic medications such as antibiotics for infections or chemotherapeutic modalities e.g. including but not limited to Adriamycin, bleomycin, Herceptin® (trastuzumab) for oncological or hematological diseases or medications such as anti-tumor necrosis factor blockers e.g. Humira® or Enbrel® (etanercept) for inflammatory diseases such as arthritis, psoriasis, eczema, Chron's disease, and ulcerative colitis.

Color detector methods according to this invention are also particularly relevant to angiotensin enzyme inhibitors (ramipril, fosinopril, lisinopril), angiotensin receptor blockers (valsartan, candesartan, losartan), Ranexa® (ranolazine), clopidogrel, ticagrelor, prasugrel, aspirin, Repatha® (evolocumab) and Parluent® (alirocumab), antibiotics (Adriamycin, bleomycin), and Herceptin® (trastuzumab).

For example, a wet run may be performed on a patient before taking a given medication, and one or more times after medication has been started, to determine the vascular improvement (if any) provided by the regimen. The color detector(s) should be in the same position on the patient for all of the tests for a consistent comparison. A greater red shift in an exercising wet run after medication has been started is indicative that the medication is having a beneficial effect on the circulatory system as a whole. When wet run results are disappointing, dose amount and/or medication type can be altered, and the resulting effect determined by another future wet run. For sedentary patients, wet run solution application combined with a "chemical" stress test can be used to gage the effect of a medication regimen. The period between color detector evaluations can be selected based on the medication, and the amount of time typically required to see the full effect. For some test treatments the second test might only be minutes or hours later. In other cases, it will be appropriate to wait for at least one day, a plurality of days, a week, or more. For example, a patient may be administered a wet run, and then started on one or more medications. A second wet run to determine cardiovascular improvement (if any) would be administered at least one day, a plurality of days, at least seven days, 1-10 days, or 5-15 days after the medication is started, and optionally repeated periodically on the same schedule.

Detecting Premature Ventricular Contractions

A premature ventricular contraction (PVC) is a cardiac event which may be experienced as a "skipped beat" or palpitations in the chest. In a normal heartbeat, the ventricles contract after the atria have contracted, which fills the ventricles. In a PVC, the ventricles contract first, before the atria have filled the ventricles with blood. This makes the heart pumping activity less effective and reduces circulation efficiency. PVC may be a sign of low oxygenation in heart muscle.

Heart electrical activity indicative of PVC can be detected by an EKG. However, PVC often only manifests sporadically. Thus, a patient suffering from PVC who is only connected to an EKG for a relatively brief period (e.g.

during a visit to a doctor's office) may not have any detectable events during that period.

PVCs reduce the heart's ability to generate sufficient blood flow throughout the circulatory system. PVC rapidly affects the color of the skin. Specifically, it briefly but detectably decreases the red color of the skin (due to the presence of less red blood in capillaries) from the normal or baseline red level. This drop-in skin redness can be detected by colorimetric means (such as a wet run) as an alternative method of diagnosing PVC without requiring an EKG machine. In particular, a patient can be fitted with a wearable color detector unit to monitor skin color for longer periods, such as for one or more days. This allows monitoring to continue for longer periods so that PVCs, if any, are likely to be detected.

Emergency Room, Intensive Care, and Surgical Theater Monitoring

Color detector monitoring can be used to continuously monitor patient cardiovascular status during high-risk situations such as in an emergency room, ambulance, intensive care unit, catheter lab, or a surgical theater. The color detector is a useful addition to known medical monitoring devices such as blood pressure monitors, pule oximeter, EKG, heart rate monitors, and the like, providing additional and confirmatory information in real-time. Color detectors' constant and immediate feedback, unlike some alternative monitoring devices (such as a blood pressure cuff) which do not provide continuous data. In one embodiment, color detector data, blood pressure, oxygenation, and heart rate are all collected and monitored simultaneously in a patient during a surgical or other medical procedure. In some instances, the color detector will provide warnings about medical problems before conventional monitoring devices because the micro circulatory environment (e.g. skin capillaries) exhibits detectable changes more quickly than the macro circulatory environment (which is correlated with conventional vital signs such as heart rate and blood pressure).

In particular, color detectors can be beneficially paired with heart rate monitors to help differentiate medical events which cause elevated heart rates based on skin red shift. Wet run monitoring is preferred, and may advantageously be performed. Cardiac output can vary independently of heart rate because of changes in stroke volume, for example (cardiac output=stroke volume X heart rate).

A patient with severe internal bleeding has increased heart rate as the body tries to compensate for dropping blood pressure due to blood loss. This is likely to be accompanied by a brief positive skin red shift (due to increased heart pumping of blood to the capillaries), followed by a sustained negative red shift (blood loss leads to less blood in capillaries).

A heart attack is characterized by increased heart rate as the heart struggles to maintain blood flow. There will be little change in skin redness levels because the increased heart rate is not effective in sustaining strong overall blood flow since portions of the heart muscle are oxygen-starved.

A patient experiencing fear or stress will exhibit both increased heart rate and positive skin red shift.

A fluctuating, up and down "sawtooth" red shift pattern is symptomatic of cardiac stress.

Consider, for example, a patient in a cardiac catheterization laboratory who is exhibiting tachycardia (elevated heart rate). There are multiple possible causes of tachycardia which require very different reactions by the clinician. If the patient is suffering from stress, pain or anxiety they will have a positive red shift. Additional anesthesia may be indicated. If the patient is bleeding they will (at least eventually) have a negative red shift. Thus, physicians may evaluate the patient for possible blood loss in response to a negative red shift.

Dry and (preferably) wet runs can also be used to detect improved circulation (i.e. positive red shift) in skin having capillaries which are downstream of a vascular intervention. For example, monitoring red shift on skin which is downstream from a stenosis and/or an artery being treated with balloon angioplasty or stent manipulation. Objective and quantified evidence is therefore provided almost immediately regarding improvements in tissue perfusion (if any) downstream of the subject artery. Color detector skin monitoring can also be used to evaluate perfusion downstream of procedures (such as vein harvesting) which could harm perfusion. Surgical methods, arrangements, and devices utilizing color detectors (including wet runs) for surgical purposes are also within the scope of the invention.

Color detector perfusion monitoring methods and devices are contemplated for tourniquet application. For example, when performing lower extremity compartmentalization for procedures such as hip replacement and knee replacement. Sufficient compression is necessary to control blood flow and blood loss. Excess pressure, however, can cause tissue damage. Color detector perfusion assessment downstream of the tourniquet can be used to determine and confirm that tourniquet pressure is not excessive, based on the presence of a threshold minimum level of perfusion (e.g. as determined by degree of negative red shift vs. baseline). This is particularly important when performing compartmentalization on a patient having peripheral artery disease or diabetes cholesterol arterial disease, which negatively affect the micro circulation of the arterial circulatory blood supply.

Color detector perfusion monitoring methods and devices are contemplated as an alternative or supplement to known blood gas evaluation means. For example, to provide continuous monitoring of blood pH, oxygen, carbon dioxide, hemoglobin, and bicarbonate levels. It is anticipated that blood characteristics such as those above are capable of calculation and derivation based on color changes in the skin. Such methods and devices are contemplated for use, for example, in continuously monitoring patient for surgery or intensive care to track homeostasis. Color detector data on one or more color traits could be fed to a device programmed to derive blood traits from the data. The derived blood traits and/or raw color detector data could in turn be displayed to an operator. A color detector device could be strapped to the arm or another accessible area with no hair or having hair removed. The patient's spectrophotometric colorimetric evaluation would continuously be input into a computer database that will monitor homeostasis and the basal metabolic environment of the tissue. This will assist the physician in adjusting medications, oxygenation, and other therapeutic inputs. It is contemplated that color detector monitoring will in some cases alert the physician to patient deterioration before other physiological parameters (e.g. blood pressure, heart rate) will.

Estimation of patient metabolic rates, including basal metabolic rates, in real time and derived from continuous color detector input, is also contemplated.

Diagnosis of arterial wall stretching during catheter procedures, hypertension, sepsis, blood loss, and hemorrhage based on skin color changes, including but not limited to red shift caused by changes in capillary blood perfusion, are also anticipated.

CPAP Machines and Obstructive Sleep Apnea

Color detector devices and methods are also relevant to diagnosing and treating respiratory conditions such as sleep apnea. Sleep apnea is a sleep disorder caused by pauses in breathing, or periods of shallow breathing, during sleep. Obstructive sleep apnea is the most common type of sleep apnea. Common symptoms include snoring, poor quality sleep, and tiredness during the daytime. Continuous positive airway pressure (CPAP) is a common treatment for severe obstructive sleep apnea.

Diagnostic tests for sleep apnea include home oximetry, or polysomnography in a sleep clinic. Pulse oximetry is a noninvasive method for monitoring oxygen saturation. A typical (transmissive) pulse oximeter is a sensor device is placed on the fingertip or earlobe. The device passes two different wavelengths of light through the body part to a photodetector. The light absorbed at the two wavelengths is used to derive blood oxygen levels. Pulse oximetry more specifically measures hemoglobin saturation. It does not monitor ventilation, and is not a complete measure of respiratory efficiency.

Continuous positive airway pressure (CPAP) devices are positive airway pressure ventilators. They are used to apply light, continuous air pressure to keep airways continuously open in people who are able to breathe spontaneously on their own. CPAP is commonly used by people who have breathing problems, such as sleep apnea. A common CPAP device includes a plastic facial mask which is connected by a tube to a small bedside CPAP machine. CPAP devices may also be used to treat premature infants whose lungs have not yet fully developed.

Color detector methods and devices can be used to monitor skin perfusion, and may, for example, be used to compliment oximeters. For example, monitoring skin red shift to identify reduced skin perfusion resulting from respiratory apnea or severe snoring. This information, in combination with additional data such as pulse oximetry, heart rate, and blood pressure, can be used to diagnose likely sleep apnea. Color detector perfusion data can be used to determine when sufficient air flow is being provided to a sleep apnea patient by a CPAP machine by confirming the absence of dips in perfusion (below baseline) caused by interrupted breathing, even while the patient is asleep. Color detector data can be used to calibrate CPAP treatments and machines. CPAP machines and respiratory diagnostic arrangements including or linked to a color detector are contemplated. For example, a CPAP machine linked to a color detector which is calibrated using color detector data to use a consistently effective air flow rate, and/or which continuously monitors patient perfusion and uses the information to automatically vary air flow. Air flow can be raised in response to low perfusion, and reduced or maintained in light of adequate or high perfusion.

In one embodiment, a physician or technician sets initial parameters for a CPAP machine and treatment. During use, skin perfusion is measured while the machine is in use (e.g. while sleeping), potentially in combination with monitoring other physiological information. The CPAP machine increases, decreases, or maintains air flow and pressure to maintain skin perfusion (derived from red shift) in a normal and desired range. In an alternative embodiment and method perfusion data (and other data) is recorded and stored during used (e.g. overnight). The data is used by the physician to analyze sleep quality, CPAP effectiveness, and/or to alter the CPAP treatment. The method and arrangement can be used to avoid inadequate and unnecessarily high (and uncomfortable) air flow during CPAP treatment.

Using an oximeter, once hemoglobin oxygen saturation has been reached, the measured oxygen level will remain at 100% regardless of how much oxygen the tissue actually has and can use. Color detector monitoring provides information on total perfusion, which importantly includes blood flow. This provides a better overall picture of that patient's respiratory status and the adequacy of CPAP treatment.

Without limitation, CPAP machines and other respiratory assistance machines which include a color detector for measuring skin perfusion based on red shift, and which calibrate or adjust air flow on that basis, are therefore within the scope of this invention. Methods of treating and diagnosing patients with respiratory conditions such as sleep apnea using color detector perfusion data are also within the scope of the invention.

Wearable Color Detectors

Skin red shift reactions can be monitored and charted over time to monitor the course of a patient's vascular health and/or the effectiveness of medication.

Wearable color detectors can be used to monitor and record skin color variation (to gauge cardiovascular health and performance) over longer periods and as they perform various activities outside of medical facilities. For example, monitoring for a plurality or hours, a plurality of days, or at least 1 hour, 5 hours, 24 hours, or 72 hours. A watch-like device analogous to a Fitbit® which performs colorimetric monitoring, for example, would be suited to this purpose. Units which also measure heart rate, distances traveled, steps, and the like could also be useful. Alternative designs could be mounted in any area of the body such as the wrist, arm, leg, or back.

Color detector monitoring can be performed during an exercise routine (e.g. with a wearable color detector) to measure the degree and duration of vascular stimulation achieved, with greater red shift indicating more stimulation. Red shift data can be applied to determine cardiovascular exertion and performance before, during, and after exercise regimens. They can also be used to measure vascular response to a given exercise regimen repeated over time, to monitor patient improvement over a period of weeks or months. This information can in turn be used to optimize exercise duration and levels for a particular individual.

Wearable color detectors preferably include mounting means for positioning at least one input for receiving light against a patient's skin for extended periods. For example, belts, wrist bands, straps, adhesives, wraps, plastic ties, or other means. Mounting means can be reversibly fixable to the patient using buckles, hook and loop fasteners, ties, an elastic band which stretches over a leg, arm, or head, and the like.

Wearable color detectors may save color data locally, or may transmit color data for storage and processing at a separate location, such as by Bluetooth, cellular, or other known methods.

Preferred wearable arrangements may incorporate both wet run chemicals and one or more color detectors positioned adjacent the same area(s) of the wearer's skin (e.g. adjacent, or within 1 or 0.5 inches), and methods using such wearable items. One embodiment is a garment including a wet run color detector adjacent a wet run carrier holding wet run chemical, and a dry run color detector at a different location. In a preferred embodiment the color detectors are positioned in the garment (e.g. a shirt) near a user's back, upper back, or shoulder blades in mirror-image locations. The garment can be shaped and sized to hold the color detectors and carrier against the skin, and/or adhesives could be used to maintain the items against the skin.

Comparing Simultaneous Red Wet & Dry Run Red Levels

Figure 11:
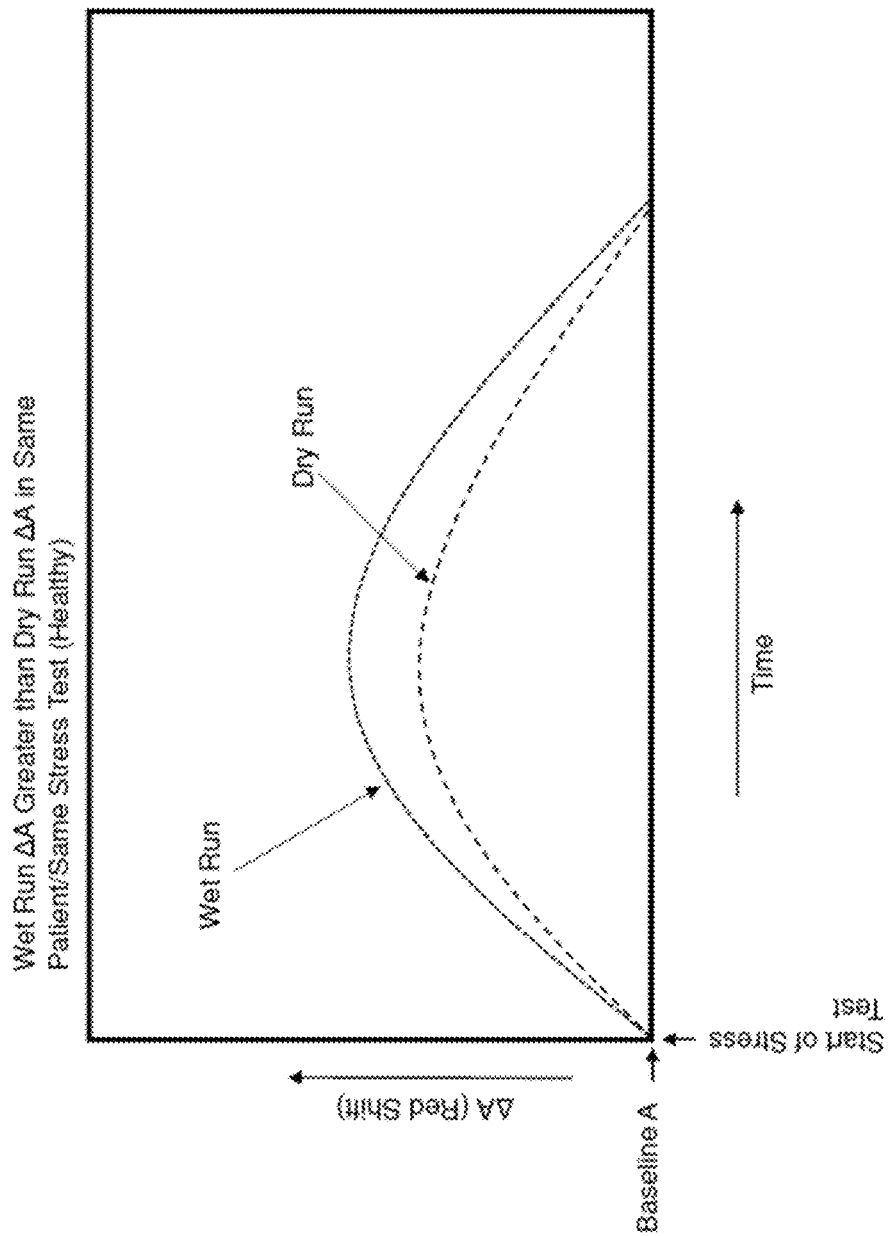
FIG. 11 is an illustrative graph of red shift data measured by wet and dry run methods during a stress test.
Figure 12:
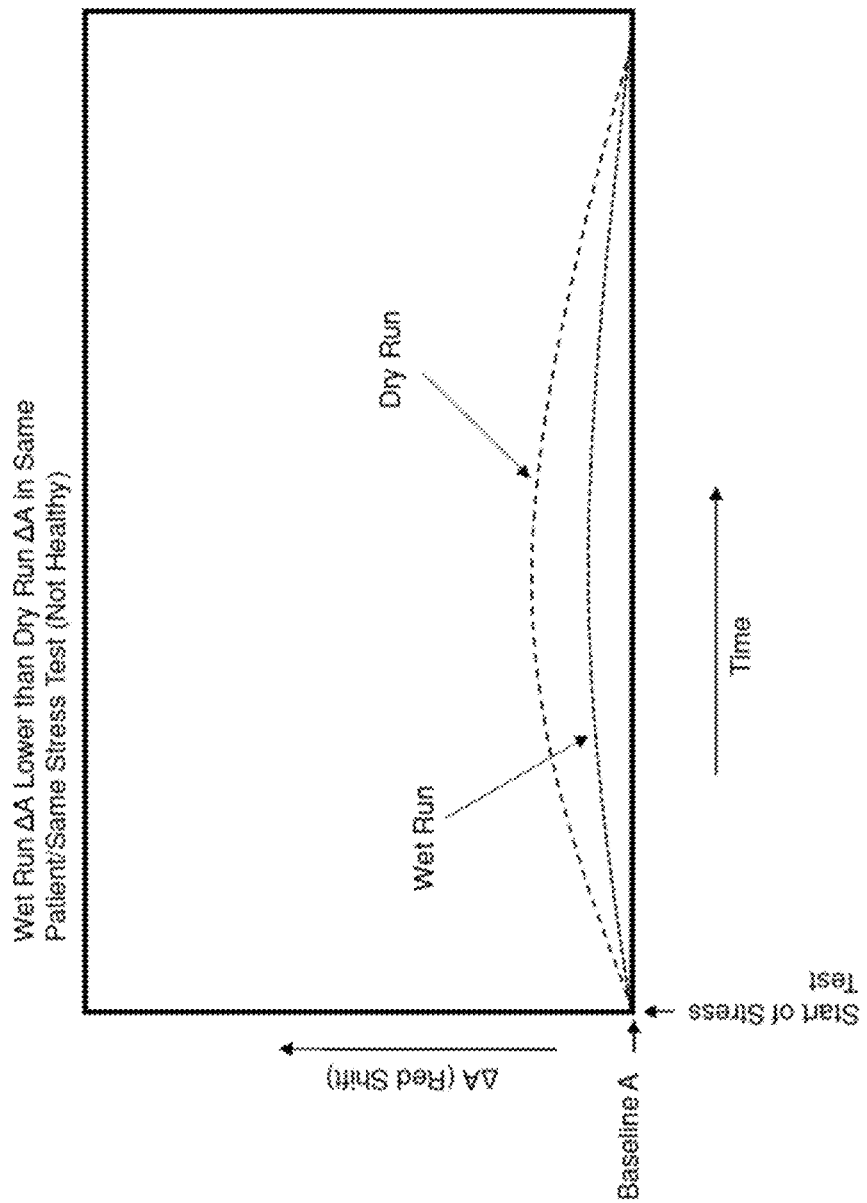
FIG. 12 is a second illustrative graph of red shift data measured by wet and dry run methods during a stress test.

It has also been found that in healthy patients, when wet run and dry run data are contemporaneously collected from a given patient over time (e.g. over the course of a single stress test), wet run red level is generally greater than dry run red level for a given patient. For example, maximum wet run red level (e.g. "a" in L/a/b scale) is at least 5% or at least 10% greater than dry run at their respective maximums or peaks, or at the wet run maximum peak. See illustrative FIG. 11. Conversely, in unhealthy patients, maximum wet run red level is generally equal to or less than dry run red levels. For example, dry run red level is equal to or greater than wet run red level, or is greater than wet run red level, at their respective peaks, or at wet run peak. See illustrative FIG. 12. Another useful yardstick is that in a healthy patient wet run redness will be greater than dry run redness over at least 60%, at least 70%, or at least 80% of the time period or time points or the tests. Further, it can be indicative of poor cardiovascular health if dry run redness is equal to or greater than wet run redness over at least 50%, at least 60%, or at least 70% of the time period or time points of a stress test.

The wet and dry run measurements are preferably taken on two different but corresponding locations (e.g. both shoulder blades, both upper arms, opposite sides of lower back, etc.) using one or, preferably, two color detectors. In a preferred approach both color detectors are strapped on or otherwise worn by the patient during an exercise regimen, although similar results can also be achieved otherwise, if less conveniently, such as by using a single color detector alternatingly on two wet and dry skin areas. Preferably the wet and dry run measurements are taken over a number of time points either simultaneously, or close in time (e.g. within 10 or 20 seconds).

Figure 13:
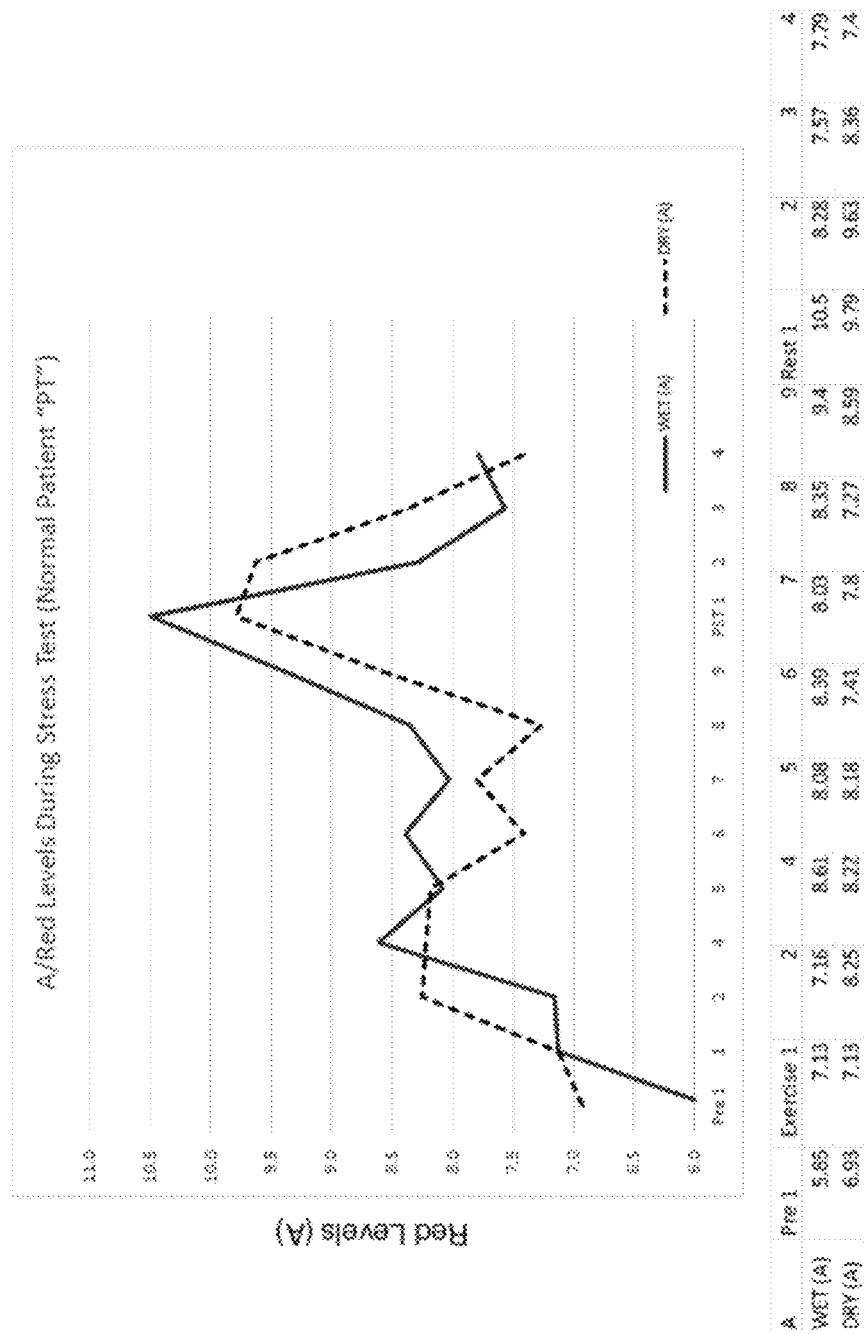
FIG. 13 is a graph and table comparing wet and dry run measurements for a normal patient during a stress test.

FIG. 13 is a curve for normal patient P. T. where the wet run peak is about 7% greater than the dry run peak.

Figure 14:
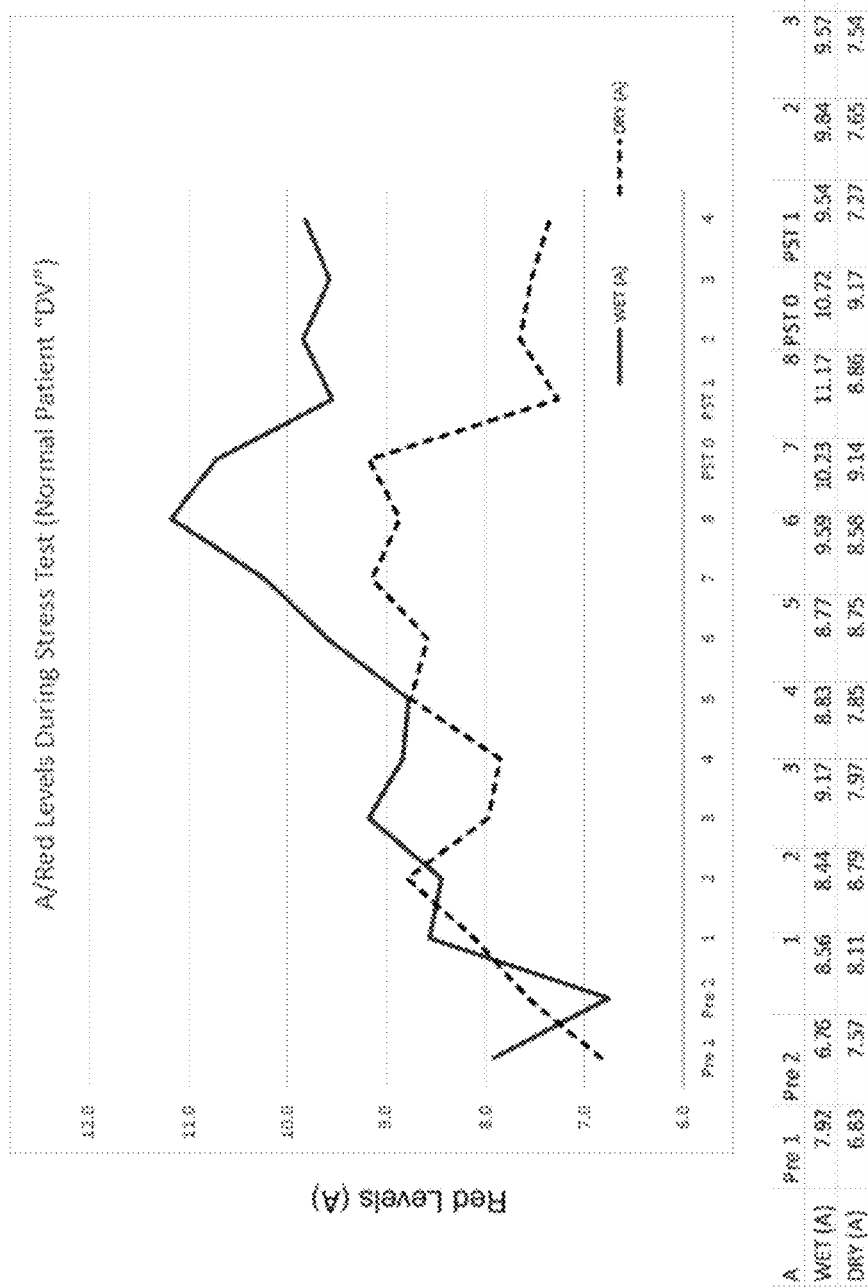
FIG. 14 is a graph and table comparing wet and dry run measurements for a second normal patient during a stress test.

FIG. 14 is a curve for normal patient D. V. having a wet run peak about 22% higher than the dry run peak, and where the wet run redness level remains above the dry run level over most of the stress test and recovery phase.

Figure 15:
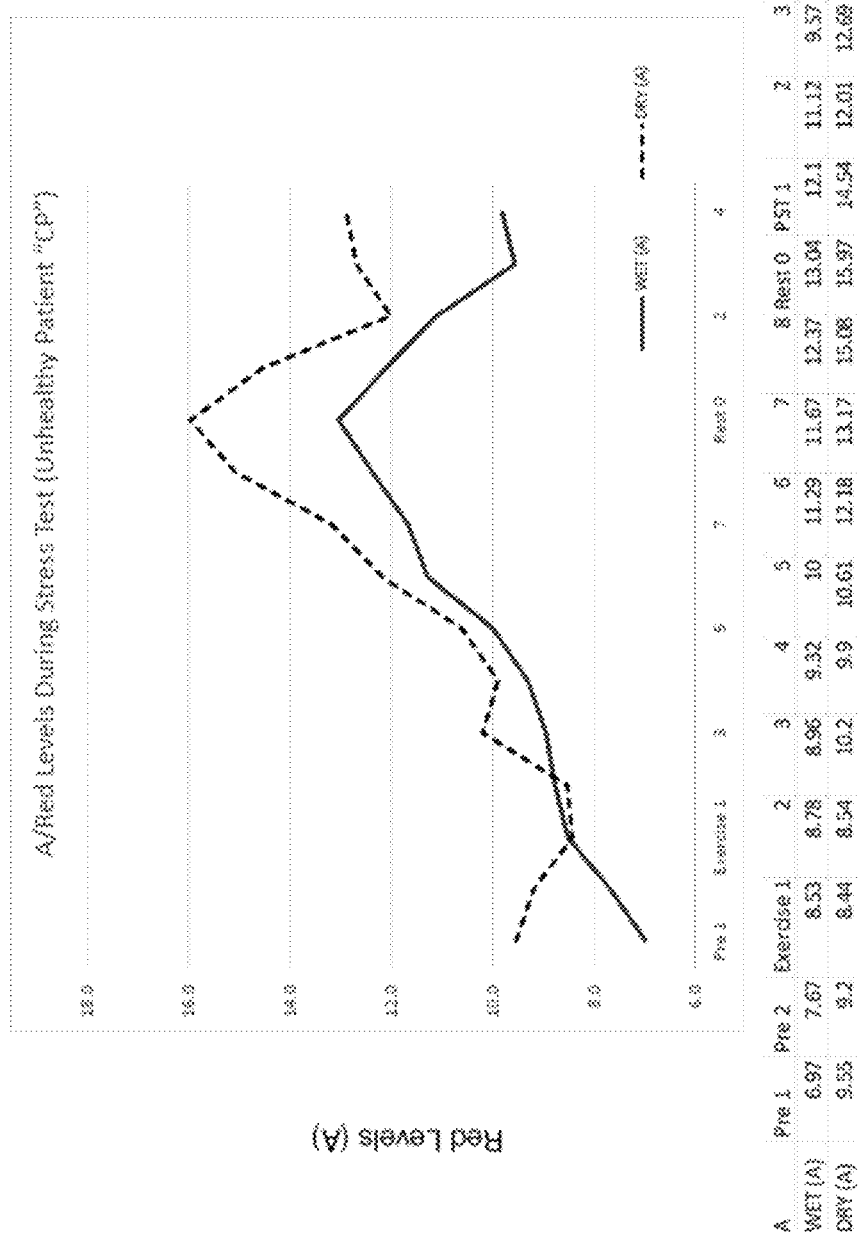
FIG. 15 is a graph and table comparing wet and dry run measurements for an unhealthy patient during a stress test.

FIG. 15 is a curve for patient C. P. where the dry run red peak is about 22% higher than the wet run peak. The dry run redness is also above wet run redness through most of the stress test. Subsequent to this test, patient C. P. was diagnosed as having ventricular tachycardia, a fast heart rate which arises from improper electrical activity in the ventricles of the heart. Ventricular tachycardia may result in cardiac arrest and turn into ventricular fibrillation.

Figure 16:
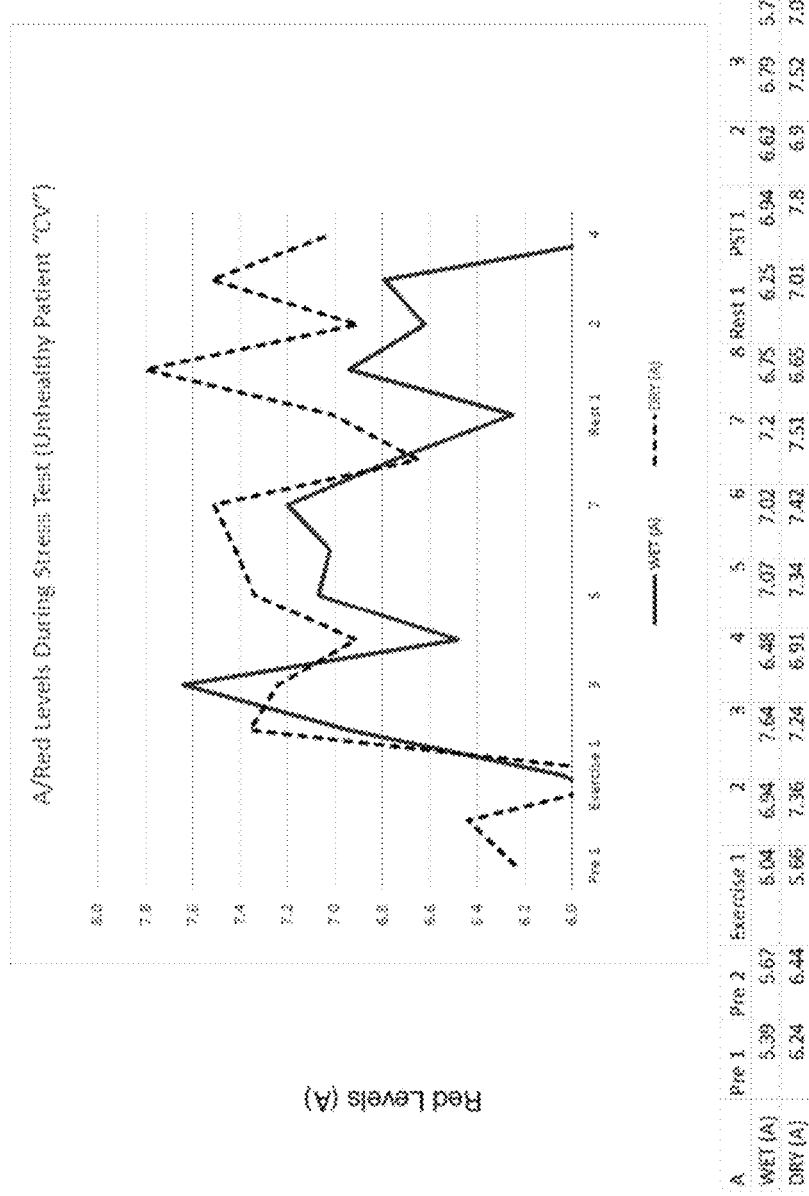
FIG. 16 is a graph and table comparing wet and dry run measurements for a second unhealthy patient during a stress test.

FIG. 16 is a curve for unhealthy patient C. V. In addition to having dry run red levels which are greater than or equal to the wet run red levels over most of the procedure and a higher dry run maximum, both the wet and dry curves have a jagged, sawtooth form which is indicative of obstructive coronary disease.

The present invention includes methods, devices, and arrangements for measuring and comparing contemporaneous wet run and dry run data from a single patient over a period of time, e.g. over the course of a stress test or other exercise regimen. In preferred embodiments two color detectors are used, one each for wet and dry runs, each positioned on corresponding but opposite skin areas (e.g. both shoulder blades, opposite sides of back, both upper arms, etc.). In preferred embodiments, both color detectors are wearable. Methods and devices which display wet run and dry run data for a patient over time (e.g. a line graph or a chart) are useful for comparing the two data sets.

While a specific embodiment of the invention has been shown and described in detail to illustrate the application of the principles of the invention, it will be understood that the invention may be embodied otherwise without departing from such principles.

What is claimed is:

1. A method for determining an efficacy of a medication for a patient, the method comprising:
   (A) administering to the patient the medication selected from the group consisting of a statin, an angiotensin enzyme inhibitor, an angiotensin receptor blocker, an antibiotic, an anti-clotting medication, ranolazine, clopidogrel, ticagrelor, prasugrel, aspirin, evolocumab, alirocumab, trastuzumab, adalimumab and etanercept;
   (B) applying a wet run solution to a testing area of a skin surface of the patient, wherein the wet run solution comprises a chemical selected from the group consisting of acetylcholine, bradykinin, adenosine, vasopressin, nitroglycerin, sildenafil, serotonin, and thrombin;
   (C) positioning a color detector on the patient after the application of wet run solution, wherein the color detector is configured for detecting at least a red wavelength light and comprises an input for receiving light, and wherein the input is positioned to receive light from the testing area;
   (D) making and saving a baseline color measurement of the testing area using the color detector, the baseline color measurement comprising a baseline skin redness level of the testing area with the patient resting;
   (E) initiating an exercise protocol after the baseline color measurement, wherein the exercise protocol comprises the patient engaging in a physical exercise;
   (F) making and saving a plurality of exercise color measurements of the testing area at different times during the exercise protocol, the exercise color measurements each comprising skin redness levels measured by the color detector;
   (G) ending the exercise protocol by the patient ending the physical exercise;
   (H) after the exercise protocol ends, beginning a recovery phase, with the patient resting during the recovery phase;
   (I) making and saving a plurality of recovery color measurements of the testing area at different times during the recovery phase, the recovery color measurements each comprising skin redness levels;
   (J) calculating the red shift for the patient, the red shift being calculated by comparing the baseline skin redness level and one of a maximum skin redness level and a minimum skin redness level, the maximum skin redness level or minimum skin redness level being selected from the exercise color measurements and the recovery color measurements; and
   (K) determining that the medication is not efficacious when a negative red shift value is calculated by comparing the baseline skin redness level with the minimum skin redness level to determine that the negative red shift value has occurred.

2. The method of claim 1, wherein the statin is selected from the group consisting of atorvastatin, rosuvastatin, simvastatin, and pravastatin, wherein the angiotensin enzyme inhibitor is selected from the group consisting of ramipril, fosinopril, and lisinopril, wherein the angiotensin receptor blocker is selected from the group consisting of valsartan, candesartan, and losartan, wherein the antibiotic is selected from the group consisting of adriamycin and bleomycin, and wherein the anti-clotting medication is selected from the group consisting of warfarin, dabigatran, rivaroxaban, apixaban, calgrelor, and cilostazol.

3. The method of claim 1, further comprising displaying on a display a graph plotting skin redness levels over a period of time, the graph comprising the baseline color measurement, at least one exercise color measurement of the plurality of exercise color measurements, and at least one recovery color measurement of the plurality of recovery color measurements.

4. The method of claim 1, wherein the exercise color measurements and the recovery color measurements are made at evenly spaced time intervals, the time intervals being between 10 seconds and five minutes; and
wherein the exercise protocol comprises increasing at least one of a speed and a resistance of the physical exercise one or more times.

5. The method of claim 1, wherein the color detector is selected from a colorimeter and a spectrophotometer.

6. The method of claim 1, wherein the wet run solution comprises acetylcholine and at least one of alcohol and water.

7. The method of claim 1, wherein the wet run solution comprises acetylcholine and at least one of petroleum jelly and an oil.

8. The method of claim 1, wherein the exercise protocol comprises the patient using at least one exercise machine selected from a treadmill, a stationary bicycle, an elliptical trainer, and an arm ergometer.

9. A method for determining an efficacy of a medication for a patient, the method comprising:
(A) administering to the patient the medication selected from the group consisting of a statin, an angiotensin enzyme inhibitor, an angiotensin receptor blocker, an antibiotic, an anti-clotting medication, ranolazine, clopidogrel, ticagrelor, prasugrel, aspirin, evolocumab, alirocumab, trastuzumab, adalimumab and etanercept;
(B) applying a wet run solution to a testing area of a skin surface of the patient, wherein the wet run solution comprises a chemical selected from the group consisting of acetylcholine, bradykinin, adenosine, vasopressin, nitroglycerin, sildenafil, serotonin, and thrombin;
(C) positioning a color detector on the patient after the application of wet run solution, wherein the color detector is configured for detecting at least a red wavelength light and comprises an input for receiving light, and wherein the input is positioned to receive light from the testing area;
(D) making and saving a baseline color measurement of the testing area using the color detector, the baseline color measurement comprising a baseline skin redness level of the testing area with the patient resting;
(E) initiating an exercise protocol after the baseline color measurement, wherein the exercise protocol comprises the patient engaging in a physical exercise;
(F) making and saving a plurality of exercise color measurements of the testing area at different times during the exercise protocol, the exercise color measurements each comprising skin redness levels measured by the color detector;
(G) ending the exercise protocol by the patient ending the physical exercise;
(H) after the exercise protocol ends, beginning a recovery phase, with the patient resting during the recovery phase;
(I) making and saving a plurality of recovery color measurements of the testing area at different times during the recovery phase, the recovery color measurements each comprising skin redness levels;
(J) calculating the red shift for the patient, the red shift being calculated by comparing the baseline skin redness level and one of a maximum skin redness level and a minimum skin redness level, the maximum skin redness level or minimum skin redness level being selected from the exercise color measurements and the recovery color measurements; and,
(K) determining that the medication is efficacious when a positive red shift value of at least +10% is calculated by comparing the baseline skin redness level with the maximum skin redness level to determine that the positive red shift value of at least +10% has occurred.

10. The method of claim 9, wherein the statin is selected from the group consisting of atorvastatin, rosuvastatin, simvastatin, and pravastatin, wherein the angiotensin enzyme inhibitor is selected from the group consisting of ramipril, fosinopril, and lisinopril, wherein the angiotensin receptor blocker is selected from the group consisting of valsartan, candesartan, and losartan, wherein the antibiotic is selected from the group consisting of adriamycin and bleomycin, and wherein the anti-clotting medication is selected from the group consisting of warfarin, dabigatran, rivaroxaban, apixaban, calgrelor, and cilostazol.

11. The method of claim 9, further comprising displaying on a display a graph plotting skin redness levels over a period of time, the graph comprising the baseline color measurement, at least one exercise color measurement of the plurality of exercise color measurements, and at least one recovery color measurement of the plurality of recovery color measurements.

12. The method of claim 2, wherein the exercise color measurements and the recovery color measurements are made at evenly spaced time intervals, the time intervals being between 10 seconds and five minutes; and
wherein the exercise protocol comprises increasing at least one of a speed and a resistance of the physical exercise one or more times.

13. The method of claim 9, wherein the color detector is selected from a colorimeter and a spectrophotometer.

14. The method of claim 9, wherein the wet run solution comprises acetylcholine and at least one of alcohol and water.

15. The method of claim 9, wherein the wet run solution comprises acetylcholine and at least one of petroleum jelly and an oil.

16. The method of claim 9, wherein the exercise protocol comprises the patient using at least one exercise machine selected from a treadmill, a stationary bicycle, an elliptical trainer, and an arm ergometer.

* * * * *